(12) United States Patent
Head et al.

(10) Patent No.: US 12,073,422 B2
(45) Date of Patent: Aug. 27, 2024

(54) METHOD, APPARATUS, AND COMPUTER-READABLE MEDIA FOR A WEB-BASED OPINION SURVEY FACTORY

(71) Applicant: HEAD RESEARCH INC., Toronto (CA)

(72) Inventors: Melinda Head, Caledon (CA); Hemant Kumar, Toronto (CA); James Andrew Wright, Liverpool (GB); Brian Blakeny Rattenbury, Toronto (CA); Martin Daniel Nathanson, Westmount (CA)

(73) Assignee: HEAD RESEARCH INC., Toronto (CA)

( * ) Notice: Subject to any disclaimer, the term of this patent is extended or adjusted under 35 U.S.C. 154(b) by 0 days.

(21) Appl. No.: 17/209,522

(22) Filed: Mar. 23, 2021

(65) Prior Publication Data
US 2021/0279748 A1 Sep. 9, 2021

Related U.S. Application Data

(63) Continuation of application No. 15/819,740, filed on Nov. 21, 2017, now abandoned.
(Continued)

(51) Int. Cl.
*G06Q 30/0203* (2023.01)
*G06F 3/04847* (2022.01)
(Continued)

(52) U.S. Cl.
CPC ..... *G06Q 30/0203* (2013.01); *G06F 3/04847* (2013.01); *G06F 3/0486* (2013.01);
(Continued)

(58) Field of Classification Search
CPC ... G06F 3/0486; G06F 3/04847; G16H 10/20; G06Q 30/0203
See application file for complete search history.

(56) References Cited

U.S. PATENT DOCUMENTS

| | | |
|---|---|---|
| 4,996,642 A | 2/1991 | Hey |
| 7,664,670 B1 | 2/2010 | Weiss |
| (Continued) | | |

OTHER PUBLICATIONS

An Intro Into Single Page Applications (SPA); as retrieved from https://blog.4psa.com/an-intro-into-single-page-applications-spa/; Mar. 12, 2013; Apps Team in Life In The Cloud (Year: 2013).*
(Continued)

*Primary Examiner* — Deirdre D Hatcher
(74) *Attorney, Agent, or Firm* — KATTEN MUCHIN ROSENMAN LLP

(57) ABSTRACT

Web-based opinion survey method, apparatus, and computer-readable media operable to cause propositional function responses to be provided to a survey server from a client device. The propositional functions are P(x), where P and x are the predicate and subject. Each P(x) is evaluated in the client device for subjects, each with a different x. Preferably, the client device displays the subjects within a Web Single Page Application (SPA) running on the client device. Preferably, the SPA displays a nonnumerical scale, the granularity of which is directly proportional to the number of pixels spanned by the scale. For each P(x), the client device displays labeled markers along the scale, to provide an indication of a level of agreement with the expressed P(x). For each P(x) subject, the client expresses an opinion on a position on the scale, whereby a pixel position corresponds to a rating for the selected subject.

8 Claims, 15 Drawing Sheets

Related U.S. Application Data

(60) Provisional application No. 62/425,944, filed on Nov. 23, 2016.

(51) Int. Cl.
| | |
|---|---|
| *G06F 3/0486* | (2013.01) |
| *G06F 16/00* | (2019.01) |
| *H04L 12/16* | (2006.01) |
| *G06F 8/20* | (2018.01) |
| *G06Q 30/02* | (2023.01) |
| *G06Q 50/26* | (2012.01) |
| *G16H 10/20* | (2018.01) |
| *H04L 51/18* | (2022.01) |

(52) U.S. Cl.
CPC .............. *G06F 16/00* (2019.01); *H04L 12/16* (2013.01); *G06F 8/20* (2013.01); *G06Q 30/02* (2013.01); *G06Q 50/26* (2013.01); *G16H 10/20* (2018.01); *H04L 51/18* (2013.01)

(56) References Cited

U.S. PATENT DOCUMENTS

| | | | |
|---|---|---|---|
| 8,577,716 B2 | 11/2013 | Bernick et al. | |
| 2002/0042718 A1 | 4/2002 | Jett | |
| 2008/0243586 A1 | 10/2008 | Dohring et al. | |
| 2010/0281355 A1 | 11/2010 | White et al. | |
| 2013/0004933 A1* | 1/2013 | Bhaskaran | G09B 7/00 434/362 |
| 2013/0179222 A1* | 7/2013 | Luth | G06Q 30/0203 705/7.32 |
| 2014/0171034 A1 | 6/2014 | Aleksin | |
| 2014/0193794 A1* | 7/2014 | Olander, III | G09B 7/06 434/362 |
| 2014/0222514 A1* | 8/2014 | Huang | G06Q 30/0203 705/7.32 |
| 2014/0278786 A1* | 9/2014 | Liu-Qiu-Yan | G06Q 30/0251 705/7.32 |
| 2014/0310062 A1* | 10/2014 | Klein | G06Q 30/0203 705/7.32 |
| 2014/0358637 A1* | 12/2014 | Kahneman | G06F 3/04847 705/7.32 |
| 2015/0262207 A1 | 9/2015 | Rao et al. | |
| 2015/0371169 A1 | 12/2015 | Ioannidis | |
| 2016/0350771 A1* | 12/2016 | Gardner | G06Q 30/0203 |
| 2018/0130075 A1 | 5/2018 | Roy | |

OTHER PUBLICATIONS

Final Office Action dated Sep. 24, 2020, from U.S. Appl. No. 15/819,740, 40 sheets.

Non-Final Office Action dated Dec. 23, 2019, from U.S. Appl. No. 15/819,740, 43 sheets.

"What is a Single Page Application"; David Diehl; Apr. 18, 2013 (Year: 2013), 8 sheets.

International Preliminary Report on Patentability completed Feb. 21, 2019, from International Application No. PCT/IB2017/001567, 21 sheets.

Sequential Bias, definition from the glossary of Insights association (formerly Marketing Research Association) retrieved from the Internet at <http://www.marketingresearch.org/issues-policies/glossary/sequential-bias> on Nov. 27, 2017.

Joel Cadwell, "Warning: Sawtooth's MaxDiff Is Nothing More Than a Technique for Rank Ordering Features!", published Jan. 14, 2013, retrieved from the Internet at <https://www.r-bloggers.com/warning-sawtooths-maxdiff-is-nothing-more-than-a-technique-for-rank-ordering-features> on Nov. 27, 2017.

R. Johnson, et al., Sawtooth Software Research Paper Series, "Adaptive Choice Based Conjoint Analysis", Sawtooth Software, 2003, retrieved from the Internet at <http://www.sawtoothsoftware.com/download/techpap/acbc.pdf> on Nov. 27, 2017.

Transmittal; International Search Report; and the Written Opinion of the International Searching Authority for International Application No. PCT/IB2017/001567, with a mailing date of Apr. 13, 2018.

\* cited by examiner

Please rate how appealing or unappealing you find the following idea: Chocolate made with milk made from sheep or goats

METHOD, APPARATUS, AND COMPUTER-READABLE MEDIA FOR A WEB-BASED OPINION SURVEY FACTORY

This application is a continuation of U.S. patent application Ser. No. 15/819,740, filed Nov. 21, 2017 which claims the benefit of provisional U.S. Patent Appln. No. 62/425,944, filed Nov. 23, 2016, the contents of all incorporated herewith.

BACKGROUND OF THE INVENTION

1. Field of the Invention

The present invention is directed to apparatus, method, and computer-readable media for Web-based opinion surveying with a broad range of applications in various fields including, but not limited to, marketing research, opinion polling, and evaluation of clinical states and outcomes.

2. Related Art

On-line opinion surveying is conducted in order to gather statistical information needed to guide the development of new products and services as well as the improvement of existing products, services and, relative to the surveying of employee satisfaction levels, working environments. It is also used to help define market segments, and to optimize the messaging crafted by marketing departments and agencies so that it resonates with the preferences of the target markets as revealed by the analysis of the survey data.

The object of opinion surveying is not limited to either products or services but could be, for instance, policy proposals being "trial-ballooned" by political parties or public advocacy organizations, or in another example, electoral options during an election campaign. Therefore in the present specification, the term "product" is used to refer to all forms of products, services, policies, including the marketing tools used or proposed for the promulgation of the foregoing, regardless of whether these products, services, policies or marketing tools already exist or are proposed new concepts, and regardless of whether they are commercial offerings, a public good, government services or the result of activities conducted by non-profit organizations.

Analysis of the survey data is intended to enable measurement of one of more of the following well-known metrics which market research seeks to establish: For new product development:
  (i) rank ordering and preference scores of multiple features of the new product;
  (ii) rank ordering for multiple proposed concepts, where each is rated according to multiple scales such as appeal, uniqueness, likelihood to purchase; and
  (iii) rating of new concepts relative to existing products (normative comparison).

For existing products:
  (i) rank ordering of customer satisfaction with a various features/aspects of an existing product:
  (ii) ratings for a range of attitudes with respect to a product, the results of which become inputs to statistical analysis for identification of market segments: and
  (iii) ratings of levels to which own brand and various competitive brands, are associated with various product attributes (serves marketing strategy for own brand, including price optimization, packaging, advertising).

For both new and existing products:
  (i) utility scores: measurement of relative importance of individual features of a product.

Finally, clinical measures, relative to some form of health care treatment; e.g. levels of wellness or suffering felt following intervention, beginning of therapy, etc.

Existing methods of conducting on-line surveying are disclosed in U.S. Pat. No. 7,664,670 ("the '670 patent"), entitled "PRODUCT DEVELOPMENT AND ASSESSMENT SYSTEM", issued to Weiss on Feb. 16, 2010 and assigned to LD Weiss, Inc., the entire contents of which are incorporated herein by reference. This patent is directed to a method, system and program product whereby survey respondents rate new products relative to one or more existing products. Respondents are prompted through a data entry terminal to rate new products relative to one or more existing products. The ratings correspond to positions chosen by the respondent along a displayed linear scale and are evaluated according to a predetermined formula applied to the scale. After an initial rating of the new product, respondents are prompted to re-assess their rating based on exposure to new information about the product which is presented on the terminal.

Based on responses to a plurality of supplementary questions about the product, an overall score is determined, preferably using a weighted average of the individual ratings for each supplementary question, which is then presented via the data entry terminal to the respondent, who is then prompted to confirm whether the result remains consistent with the initial assessment.

Various embodiments of the methods and apparatus disclosed in the '670 patent can be used for all of the aforementioned metrics. However, as described below, there are limitations to the accuracy of the ratings and preference rankings that can be obtained using these methods.

From the perspective of quantitative market research practice, one notable weakness of the existing on-line surveying methods is statistical bias. Bias is introduced into the results of a survey as a consequence of two different characteristics of these methods. First, when respondents' ratings are transformed into numerical values, computed according to a pre-determined scale, the potential exists not only for information to be lost in the transformation, but also for the values to be skewed by bias in the survey designer's choice of scale. Furthermore, using a weighted average to compute an overall score imposes an additional bias in terms of the weighting assigned to individual features which respondents are asked to rate. Ideally, an unbiased methodology is required for establishing the value of the weightings. The '670 patent does not disclose any methodology for this, unbiased or otherwise.

Finally, when respondents are prompted to re-assess their rating of a product in view of the overall score computed from the ratings for individual features, the potential is established for compounding the bias, already built into the overall score, in terms of the responses elicited from respondents.

The second characteristic producing bias is the "order bias" or "sequential bias", which are inherent in the process of responding to the survey questionnaire. The Market Research Association (1156 15th Street NW, Suite 302, Washington, DC 20005) provides the following definition of sequential bias, currently available at the URL http://www-.marketingresearch.org/issues-policies/glossary/sequential-bias and titled: "When respondents tend to favor objects because of their position in a list or sequence. The objects at the beginning and at the end of a list can be remembered more than those occurring in the middle. Usual practice is to rotate a list to eliminate this type of bias", the entire contents of which are incorporated herein by reference.

By randomizing the degree of rotation so that a questionnaire is equally likely to be started at any point in the list, sequential bias is distributed across the elements in the list. This approach offsets the statistically aggregate effect of sequential bias, but does not counteract the tendency toward bias which is inherent in the process of a single respondent proceeding through a questionnaire. In other words, randomization does not reduce the aggregate bias of all the respondents as they fill out a questionnaire, but rather spreads the bias with the expectation that by evenly distributing it among the respondents, its net effect is cancelled.

Such an expectation has certain drawbacks. For instance, if any aspect of the statistical analysis of survey data is aimed at determining market segmentation, it would be desirable to ensure that sequential bias is equally reflected in each demographic cohort represented in the sample of respondents and therefore the randomization should take that into account.

It is axiomatic that the root of bias affecting the results of survey data is the variability in the cognitive and emotional processes that govern an individual respondent while answering an on-line questionnaire. For instance, even if there is a known tendency for sequential bias, the degree of sequential bias exhibited by an individual respondent may vary from the expected behavior due to subjective factors which are by definition, un-measurable. It is therefore a basic tenet of the present specification that the potential for bias should be minimized at its source, which is the interaction of the respondent with the survey. It is the robustness, flexibility and ultimately the perceived intuitiveness of the Human-Machine Interface (HMI), which can best reveal a respondent's true preferences.

It should also be recognized that the source of order bias in the existing opinion surveying art, where an array of options must be ranked, is the implicit assumption that the survey is to be conducted by introducing each element in the array sequentially. Even if the elements in the array are randomly reordered prior to their presentation to an individual respondent, the respondent is nevertheless restricted to learning about these options one at a time. Furthermore, since the effect of bias may vary between individuals (e.g. some individuals may be cognitively inclined to favor paying more attention to the earlier options and some may deliberately lean in the other direction), randomization is not a guaranteed path to elimination of bias, but rather to an unknown re-distribution of bias. The present invention discloses a method which further reduces the potential for order bias by avoiding the need for sequential presentation of the elements in an array of options.

In addition to the presence of statistical bias, it can also be argued that there are methodological shortcomings in the existing art. For example, to determine the "rank order and preference scores" metric, one of the most prevalent methods is based on the concept of "MaxDiff", which assumes that eliciting accurate measures of preference is most likely when respondents are asked to select, from within a larger set, the pair of items that reflects the most and least preferred. By presenting respondents with a series of strategically designed sub-sets and asking them to select the" MaxDiff pair for each, the full ranked order of all the items in the larger set can be revealed. This obviates the need to require explicit comparison of all possible pairs in the larger set (the number of which, for n items, is=n!/((n−2)!*2!)).

This approach is also used to derive preference scores in terms of how many times one item is chosen over another. However, the accuracy and value of preference scores derived in this manner are suspect, because the rank ordering on which the scores are based does not provide a quantitative measurement of the importance of each item. A detailed critique of this methodology, in the context of one commercial implementation of it, is in an article "Warning: Sawtooth's MaxDiff Is Nothing More Than a Technique for Rank Ordering Features!", Joel Cadwell in R-Bloggers, Jan. 14, 2013, which can be found at the URL: https://www.r-bloggers.com/warning-sawtooths-maxdiff-is-nothing-more-thana-technique-for-rank-ordering-features, the entire contents of which are incorporated herein by reference.

There are also methodological debates surrounding the metric of "utility scores." The existing practice of "conjoint analysis" attempts to measure the "utility" which a respondent gets from an existing product feature (or expects to get from a potential new feature). These measures are based on statistical analysis of data obtained by surveys which elicit preferences with respect to various combinations of features in new or existing products. The combinations of features ("profiles") presented to respondents are the result of what is called "choice set design", a process aimed at reducing the number of possible profiles to a level which can be managed within a reasonable amount of time.

Practitioners of conjoint analysis have proposed statistical methods whereby the "choice set design" is incrementally improved based on previous results (see, for example, the article: "Sawtooth Software", Research Paper Series, Adaptive Choice Based Conjoint Analysis", R. Johnson, et al., Sawtooth Software, 2003, and available at http://www.sawtoothsoftware.com/download/techpap/acbc.pdf), the entire contents of which are incorporated herein by reference. As explained below with respect to the present embodiments, in the case with "rank order and preference scoring", the use of a scale where granularity of measurement is limited only by the pixel density of the display, provides a mechanism for collecting data that leads to the design of better choice sets.

In addition to the seven aforementioned metrics, market survey data is also used to establish a "Net Promoter Score" or NPS, which measures the aggregate willingness of customers to recommend a product or service. The precision of the NPS is a function of the granularity of the scale on which respondents' ratings are measured. In much of the existing art, discrete scales are used with a limited number of possible values. If a highly granular scale offers, say, 100 points of value between two contiguous values on a very discrete scale, use of the latter can result in loss of information such that the true value of the NPS is not captured.

Existing market survey methodology is also constrained by the application of depersonalized norms to all respondents. When a survey is designed for normative comparisons, where a new product or service is rated relative to an existing one, different respondents may have substantially different perceptions of what constitutes a desirable improvement between an incumbent product/service and a new proposed offering. For one respondent, a specific linear displacement along the rating scale may represent only a marginal improvement, whereas for another respondent the same linear displacement may be extremely attractive. In such instances, these distinctions cannot be revealed because the same norms are applied to all respondents. This deficiency can be mitigated by segmenting respondents into categories based on similar measures of what constitutes "improvement."

The existing art is also constrained by the communications architecture underlying the Web-based systems which provide on-line opinion surveying capabilities (e.g. Survey- Monkey, Qualtrics, etc.) support a relatively small number of respondents, typically in the range of several hundred and in some circumstances several thousand. In instances where it is possible and preferable to support a much larger number of concurrent respondents, too many clients trying to access the database simultaneously can result in a breakdown of the system on the server side: e.g. national opinion polling on the Web site of a TV news network following a major televised event, news conference, speech, etc. The present invention discloses the methods whereby the proficient use of an advanced Web development platform enables the number of respondents to be scaled to unprecedented levels.

In the Internet era, extremely large-population surveys (e.g., elections) may be taken quickly (in as little as a few hours), given the wide prevalence of personal computing devices (PCs, smartphones, laptops, etc.). However, a problem in such large-population surveys is how to accurately discriminate different gradations of responses. Providing a color palette of possible responses gives a very wide range of gradations, with the mere sliding of a mouse (for example) providing an almost infinite array of gradations. Rapid, large-population surveys providing such gradations were not possible before the Internet age. In order to make such survey results valid, the colors of the pixels projected onto the displays should be relatively uniform. Thus, the choice of the colors and their gradations is a non-trivial matter.

SUMMARY OF THE INVENTION

The present invention is related to a Web-based application software package developed to enable the rapid creation of opinion surveys that overcome the limitations of existing on-line market research techniques. It preferably provides a robust and intuitive user interface, designed to expose options to survey respondents such that the potential for bias in their choices and preference ratings in minimized. These user interfaces preferably provide Single Page Applications (SPAs), and are preferably implemented using the MEAN (Mongo DB, Express.js, Angular.js and Node.js) Web development framework which is well suited to SPAs.

Avoiding the conventional use of rating scales based on discrete, and arguably arbitrary values for measuring preference or opinion, a preferred embodiment uses the pixel density of the scale (along which respondents rate products, services, features, etc.) to define the granularity of the ratings. A preferred embodiment relies extensively on graphical elements to facilitate the conceptualization of the competing, or alternative, products, services, features, etc. which respondents are asked to rate and to compare. By enabling all options to be presented simultaneously within a single "palette" section of the Web page, and allowing the respondent to drag, from the palette, icons which are representative of the options, and to drop them onto the rating scale, the preferred embodiments minimizes the potential for order bias to skew respondents' expression of preference. The user interface also enables the rearrangement of the rank order of an array of options by enabling the respondent to slide the icon corresponding to any option to any new position on the scale, a capability which provides unlimited potential for a change of opinion after reflection on the comparative preference for all the options visually displayed along the scale.

According to a first aspect according to the present invention, a Web-based opinion survey server apparatus is operable to cause a plurality of propositional function responses to be provided from at least one client device. The propositional functions are preferably expressed as P(x), where P and x are respectively the predicate and the subject of said P(x), where each said P(x) is evaluated in the at least one client device for a plurality of subjects, each with a different value of x. Preferably, the predicate and the plurality of subjects are pre-configurable on the at least one survey server. The at least one survey server preferably has at least one memory storing program code, and at least one processor executing the program code to cause the at least one survey server to perform at least one process for each said P(x), such as: (i) causing the at least one client device to display on at least one client device display the each P(x) plurality of subjects, within a Web Single Page Application (SPA) running on the at least one client device: (ii) causing the SPA to display on the at least one client device display a non-numerical scale of which a measure of granularity is directly proportional to the number of pixels spanned by the scale, where for screen sizes >=1200 pixels the scale uses 1000 pixels, for screen sizes >=991 and <1200 pixels, the scale uses 750 pixels, for screen sizes <=600 and <991 pixels, the scale uses 500 pixels and for screen sizes <600 pixels, the scale uses 250 pixels: (iii) for each P(x) plurality of subjects, causing the at least one client device to display on the at least one client device display a plurality of pre-configurable labeled markers along the scale to provide an indication on the scale of a relative level of agreement with, or preference for, the proposition expressed by the corresponding P(x); (iv) for each P(x) plurality of subjects, causing the at least one client device to enable at least one client to express opinion on a position on the scale using at least one input device of the at least one client device, whereby a pixel position corresponding to the position of the client input selection comprises a rating for the selected subject: and (v) for each P(x) plurality of subjects, recording said rating in the at least one survey server at least one memory.

According to a second aspect according to the present invention, a Web-based opinion survey server method is operable to cause a plurality of propositional function responses to be provided from at least one client device. The propositional functions expressed as P(x), where P and x are respectively the predicate and the subject of said P(x), where each said P(x) is evaluated in the at least one client device for a plurality of subjects, each with a different value of x, wherein the predicate and the plurality of subjects are pre-configurable on the at least one survey server. The at least one survey server has at least one memory storing program code, and at least one processor executing the program code to cause the at least one survey server to perform the method of: (i) the at least one client device displaying on at least one client device display the each P(x) plurality of subjects, within a Web Single Page Application (SPA) running on the at least one client device: (ii) the SPA displaying on the at least one client device display a non-numerical scale of which a measure of granularity is directly proportional to the number of pixels spanned by the scale: (iii) for each P(x) plurality of subjects, the at least one client device displaying on the at least one client device display a plurality of pre-configurable labeled markers along the scale to provide an indication on the scale of a relative level of agreement with, or preference for, the proposition expressed by the corresponding P(x): (iv) for each P(x) plurality of subjects, the at least one client device enabling at least one client to express opinion on a position on said scale using at least one input device of the at least one client device, whereby a pixel position corresponding to the position of the client input selection comprises a rating for the selected subject: and (v) for each P(x) plurality of subjects, recording said rating in the at least one survey server at least one memory.

According to a third aspect according to the present invention, at least one non-transitory computer-readable medium storing program code which causes at least one processor in a Web-based opinion survey server to perform functions operable to cause a plurality of propositional function responses to be provided from at least one client device, the propositional functions expressed as P(x), where P and x are respectively the predicate and the subject of said P(x), where each said P(x) is evaluated in the at least one client device for a plurality of subjects, each with a different value of x, wherein said predicate and said plurality of subjects are pre-configurable on the at least one survey server, the at least one survey server having at least one memory storing said program code, the at least one processor executing said program code to cause the at least one survey server to perform the functions of: (i) the at least one client device displaying on at least one client device display the each P(x) plurality of subjects, within a Web Single Page Application (SPA) running on the at least one client device: (ii) the SPA displaying on the at least one client device display a non-numerical scale of which a measure of granularity is directly proportional to the number of pixels spanned by said scale: (iii) for each P(x) plurality of subjects, the at least one client device displaying on the at least one client device display a plurality of pre-configurable labeled markers along said scale to provide an indication on said scale of a relative level of agreement with, or preference for, the proposition expressed by the corresponding P(x): (iv) for each P(x) plurality of subjects, the at least one client device enabling at least one client to express opinion on a position on said scale using at least one input device of the at least one client device, whereby a pixel position corresponding to the position of the client input selection comprises a rating for the selected subject: and (v) for each P(x) plurality of subjects, recording said rating in the at least one survey server at least one memory.

DETAILED DESCRIPTION OF THE PRESENTLY PREFERRED EXEMPLARY EMBODIMENTS

Glossary

Figure 1:
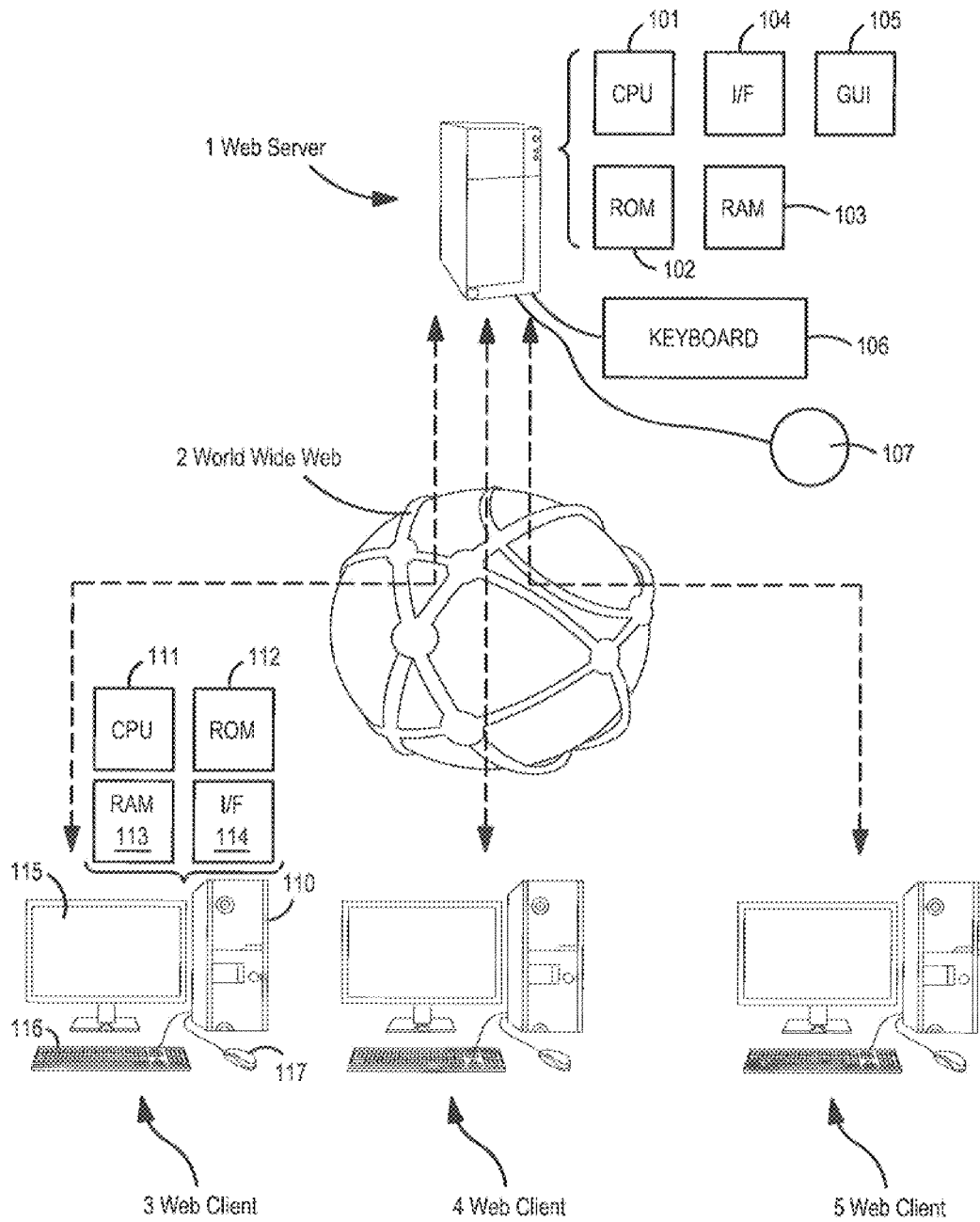
FIG. 1 is a schematic hardware block diagram according to a preferred embodiment of the present invention.

List of Definitions $scope. $scope is a Javascript software object created by the Angular.js Web development framework to encapsulate the Model data of the Angular application.

AJAX. AJAX is a set of web development techniques using many web technologies on the client-side to create asynchronous Web applications. With Ajax, web applications can send data to and retrieve from a server asynchronously without interfering with the display and behavior of the existing page. By decoupling the data interchange layer from the presentation layer, Ajax allows for web pages, and by extension web applications, to change content dynamically without the need to reload the entire page. In practice, modern implementations commonly substitute JSON for XML due to the advantages of being native to JavaScript.

Angular.js. HTML is used for declaring static documents, but it falters when used for declaring dynamic views in web-applications. AngularJS is code to extend HTML vocabulary for an application. The resulting environment is expressive, readable, and quick to develop.

Client-side. The programs running on the Web Server are server side programs because they are on the side of the internet that the Web server is on. The browser being used to access the Web site is on the same side of the Web as you, the client side. If code is executed on the Web server, it is considered server side code.

Express.js. is the Web application framework for Node.js which corresponds to the "backend" part of the MEAN stack or software bundle.

ECMAScript. (or ES) is a scripting-language specification standardized by Ecma International in ECMA-262 and ISO/IEC 16262. It was based on JavaScript, which now tracks ECMAScript. It is commonly used for client-side scripting on the World Wide Web. Other implementations of ECMAScript include Jscript and ActionScript.

Javascript. JavaScript is a high-level, dynamic, untyped, and interpreted programming language.Alongside HTML (Hyper Text Markup Language) and CSS (Cascading Style Sheets), it is one of the three core technologies of World Wide Web content production: the majority of websites employ it and it is supported by all modern Web browsers without plug-ins.

JQuery. jQuery is a fast, small, and feature-rich JavaScript library. It makes things like HTML document traversal and manipulation, event handling, animation, and Ajax much simpler with an easy-to-use API (Application Programming Interface) that works across a multitude of browsers. With a combination of versatility and extensibility, jQuery has changed the way that millions of people write JavaScript.

MONGO DB. MongoDB (from humongous) is a Free and open-source cross-platform document-oriented database program.

Node.js. Node.js is an open-source, cross-platform JavaScript runtime environment for developing a diverse variety of tools and applications. Although Node.js is not a JavaScript framework, many of its basic modules are written in JavaScript, and developers can write new modules in JavaScript. The runtime environment interprets JavaScript using Google's V8 JavaScript engine.

Order bias. See above.

Palette. An array of indicia: in the present embodiments, usually one or more color palettes which display a plurality of different color indicia, among which a user can choose.

Predicate. The non-variable component of a propositional function.

Propositional function. A statement, formulated in mathematical logic, comprising a predicate and a variable component called the "subject", The statement is expressed as a question, the answer to which constitutes the evaluation of the function.

Server-side. Server-side (commonly referred to as SS) refers to operations that are performed by the server in a client-server relationship in a computer network. Typically, a server is a computer program, such as a web server, that runs on a remote server, reachable from a user's local computer or workstation.

Subject. The value of the variable in a propositional function.

A "device" in this specification may include, but is not limited to, one or more of, or any combination of processing device(s) such as a cell phone, a Personal Digital Assistant, a smart watch or other body-borne device (e.g., glasses, pendants, rings, etc.), a personal computer, a laptop, a pad, a cloud-access device, and/or any device capable of sending/receiving messages to/from a local area network or a wide area network (e.g., the Internet), such as devices embedded in cars, trucks, aircraft, household appliances (refrigerators, stoves, thermostats, lights, electrical control circuits, the Internet of Things, etc.).

An "engine" is preferably a program that performs a core function for other programs. An engine can be a central or focal program in an operating system, subsystem, or application program that coordinates the overall operation of other programs. It is also used to describe a special-purpose program containing an algorithm that can sometimes be changed. The best known usage is the term search engine which uses an algorithm to search an index of topics given a search argument. An engine is preferably designed so that its approach to searching an index, for example, can be changed to reflect new rules for finding and prioritizing matches in the index. In artificial intelligence, for another example, the program that uses rules of logic to derive output from a knowledge base is called an inference engine.

As used herein, a "server" may comprise one or more processors, one or more Random Access Memories (RAM), one or more Read Only Memories (ROM), one or more user interfaces, such as display(s), keyboard(s), mouse/mice, etc. A server is preferably apparatus that provides functionality for other computer programs or devices, called "clients." This architecture is called the client-server model, and a single overall computation is typically distributed across multiple processes or devices. Servers can provide various functionalities, often called "services", such as sharing data or resources among multiple clients, or performing computation for a client. A single server can serve multiple clients, and a single client can use multiple servers. A client process may run on the same device or may connect over a network to a server on a different device. Typical servers are database servers, file servers, mail servers, print servers, web servers, game servers, application servers, and chat servers. The servers discussed in this specification may include one or more of the above, sharing functionality as appropriate. Client-server systems are most frequently implemented by (and often identified with) the request-response model: a client sends a request to the server, which performs some action and sends a response back to the client, typically with a result or acknowledgement. Designating a computer as "server-class hardware" implies that it is specialized for running servers on it. This often implies that it is more powerful and reliable than standard personal computers, but alternatively, large computing clusters may be composed of many relatively simple, replaceable server components.

The servers and devices in this specification typically use the one or more processors to run one or more stored "computer programs" and/or non-transitory "computer-readable media" to cause the device and/or server(s) to perform the functions recited herein. The media may include Compact Discs, DVDs, ROM, RAM, solid-state memory, or any other storage device capable of storing the one or more computer programs.

List of Acronyms

AJAX, Asynchronous, Javascript, XML (XML—Extensible Markup Language)

JSON. (JavaScript Object Notation) is a lightweight data-interchange format. It is easy for humans to read and write. It is easy for machines to parse and generate.

MEAN. Mongo DB, Express.js, Angular.js and Node.js

MVC. Model-View-Controller

NPS, Net Promoter Score

OOD. Object-Oriented Design

OOP. Object-Oriented Programming

SPA. Single Page Application

URL. Uniform Resource Locator.

The present embodiments provide methods, apparatus, and a comprehensive system designed as a re-usable software platform for enabling the construction of program products for Web-based Opinion Surveys. As such, they correspond in principle to the paradigm of a software design pattern known in the software industry as a "factory", and is henceforth referred to in this disclosure as the Web-based Opinion Survey Factory ("factory"). The preferred embodiments of the factory are built using an open-source software bundle entitled MEAN, which is an acronym representing the four components of the bundle: Mongo DB, Express.js, Angular.js and Node.js. This is a comprehensive Web development framework providing a rich set of tools for creation of "Single Page Applications" (SPA). SPA's are Web applications which require little or no reloading of the Web page from the server-side of the communications link in order to effect the requisite changes to the page resulting from user input. In an SPA implemented with the MEAN framework, the interaction triggered by the user between the application code and the page occurs on the client-side of the communications link.

FIG. 1 is a schematic hardware block diagram according to a preferred embodiment of the present invention. Web Server 1 is preferably a computer platform with at least one processor running the Mongo DB, the access to which is implemented in Node.js within the Express.js server-side development framework. Web Server 1 preferably comprises at least one processor 101, non-transitory computer-readable media such as ROM 102 and/or RAM 103, one or more wired and/or wireless interfaces 104, and (optionally) a Graphical User Interface 105 (GUI: e.g., a monitor screen), keyboard 106, and mouse 107. Preferably, computer program code (to be discussed below) is stored in the computer readable media and runs on the one or more processors and causes the Web Server 1 to perform the functions and/or steps described below. Web Server 1 is preferably coupled and/or connected to one or more Web Clients (3,4,5 and so on) through the medium of the World Wide Web 2. Each of the Web Clients preferably comprises a computer platform (e.g., a personal computer 110, a pad, a smart phone, and/or a Personal Digital Assistant, etc.) having at least one processor 111, non-transitory computer-readable media such as ROM 112 and/or RAM 113, one or more wired and/or wireless interfaces 114, and a GUI 115, keyboard 116, and mouse 117. Preferably, each Web Client runs at least one Web browser, such as Internet Explorer, Firefox, Chrome, etc., enabled to support Angular.js scripts embedded in the HTML pages served by Web Server 1.

Figure 2:
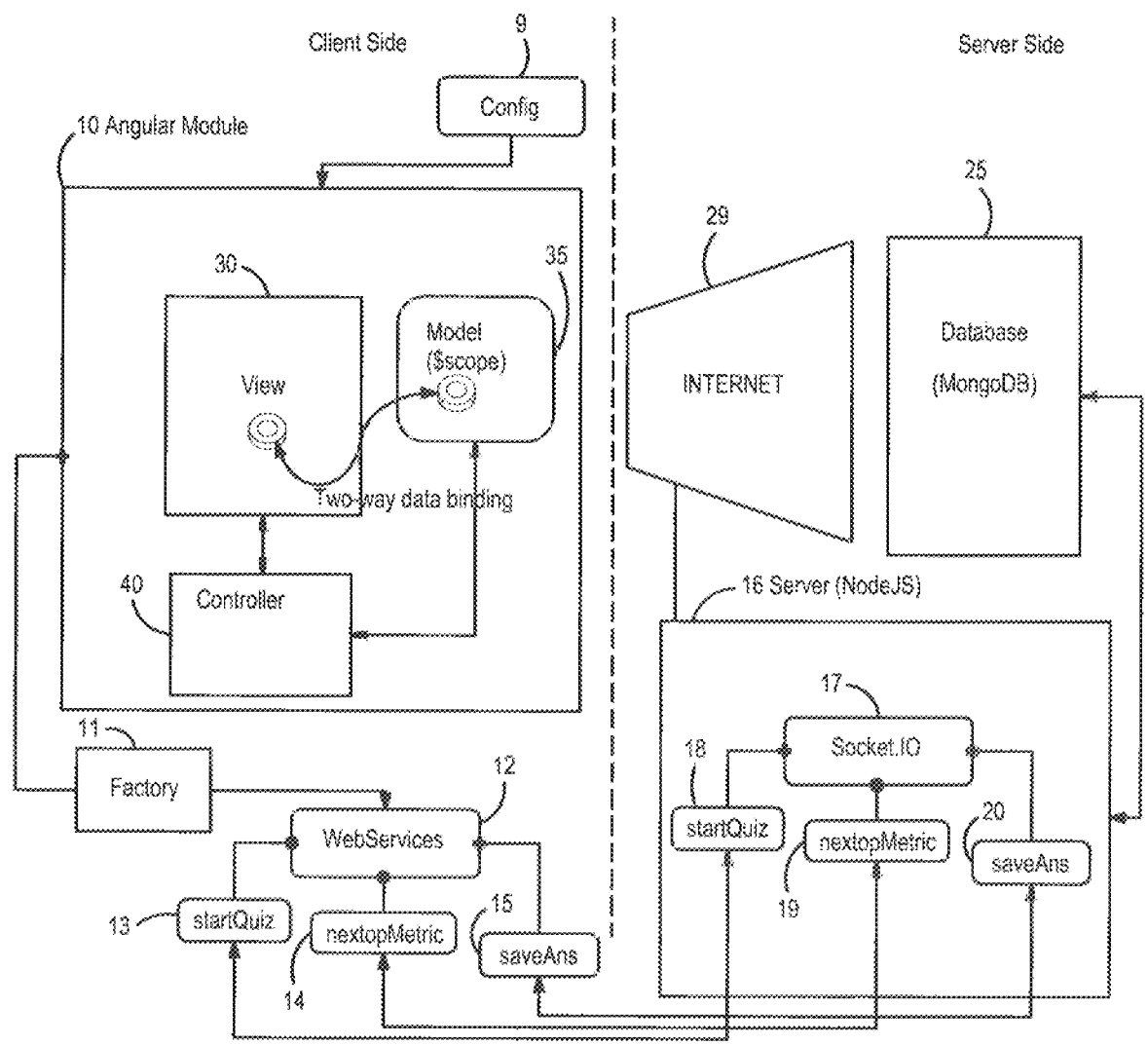
FIG. 2 is a schematic functional diagram showing certain functional aspects, such as the Model-View-Controller (MVC) architecture with MEAN framework according to the FIG. 1 embodiment.

The client-side of the MEAN bundle preferably comprises Angular.js, a Javascript (JS) derivative that enables a client-side framework for a Model-View-Controller (MVC) architecture on which the factory design is based. FIG. 2 illustrates this architecture in the context of its application to the MEAN Web development framework.

A notable feature of the Angular.js is the concept of "two-way data binding." In brief, this concept enables elements within the "View" component of the MVC architecture (what the client sees on his Web browser) to be paired with specific objects in the Model component (of the MVC architecture, which encompasses the data structures for the software application logic that manipulates them. This pairing is a bi-directional relationship that enables changes on one side to be immediately reflected on the other. Two-way data binding largely relieves the server backend of templating responsibilities. Instead, templates are rendered in plain HTML according to data contained in a scope defined in the model. The $scope service in Angular detects changes to the model section and modifies HTML expressions in the view via a controller. Likewise, any alterations to the view are reflected in the model.

The design of the Model component of the MVC architecture meets the basic requirements of the factory, which are to produce Web-based Opinion Surveys as specified above. The building blocks of the Model are "objects", a term adopted for the purpose of this disclosure from the prevailing paradigm of Object-Oriented Design (OOD) and Object-Oriented Programming (OOP), the prevailing paradigm in software language development, software-based systems design, and application programming. Objects are defined as the data elements, and their associated behavior in terms of changes in value, when processed by the software application logic under the various conditions created by user (client-side) input. Objects can acquire the behavioral characteristics of other objects, known as "inheritance", which allows the OOP developer to re-use software application logic without having to replicate the code. In other words, if the logic governing the behavior of an object under specific conditions is identical to that of another object, inheritance enables the functionality of the latter to be invoked when the former is subject to those specific conditions.

As depicted in FIG. 2, the Model 35 component of the MVC architecture, which can alternatively be described as the "$scope" object, is created automatically by Angular.js. The $scope object is passed as a parameter to the standard process within Angular.js which constructs the Controller (code) depicted in FIG. 2 as component 40 of the MVC architecture. As such, Controller 40 inherits the functions and properties of the $scope and adds the user-developed functions specific to the application. All of the MVC components are contained within the Angular "Module" 10. All Angular.js application packages are initialized within a software component called a "Module", which is effectively a "container" object that encompasses the other components, as illustrated in FIG. 2. The Angular.js framework provides a library of services, or "methods", which are invoked, using specified Application Programming Interface (API) calls, to configure the Module. These methods are:

(i) "Config", depicted as function 9 in FIG. 2. This provides Module 10 with a deep-linked URL, i.e. a hyperlink to the specific page operating the Opinion Survey, within the larger website of the sponsor or business entity conducting the survey, to which it is routed on initialization.

(ii) "Factory", labeled as function 11 in FIG. 2, the purpose of which is to create the WebServices object 12, comprising the functions:

(i) startQuiz 13
      (ii) nextOpMetricInfo 14
      (iii) saveAns 15

These functions use the Web support services built into the Angular.js framework for communicating with the server-side in order to, respectively:

(i) initiate the survey.
   (ii) retrieve the questionnaire information required in order to acquire the next "opinionMetric" (the definition of which is provided below) in the survey.
   (iii) commit the respondent's answers to the back-end (server-side) database 25.

The View and Model components of the MVC, labeled 20 and 35, are described above.

Server object 16, is a software application, implemented using Node.js, to provide the interface to the database 25 on the server-side of the Web communications link which is represented in FIG. 2 as the socket connection 17, and the WebServices functions 13, 14 and 15 communicate with, respectively, peer functions 18, 19 and 20 which are part of Server 16. The operations of the elements of FIG. 2 will, be described in greater detail below. Server 16 couples to the telecommunications network (e.g., the Internet) 24.

Figure 3A:
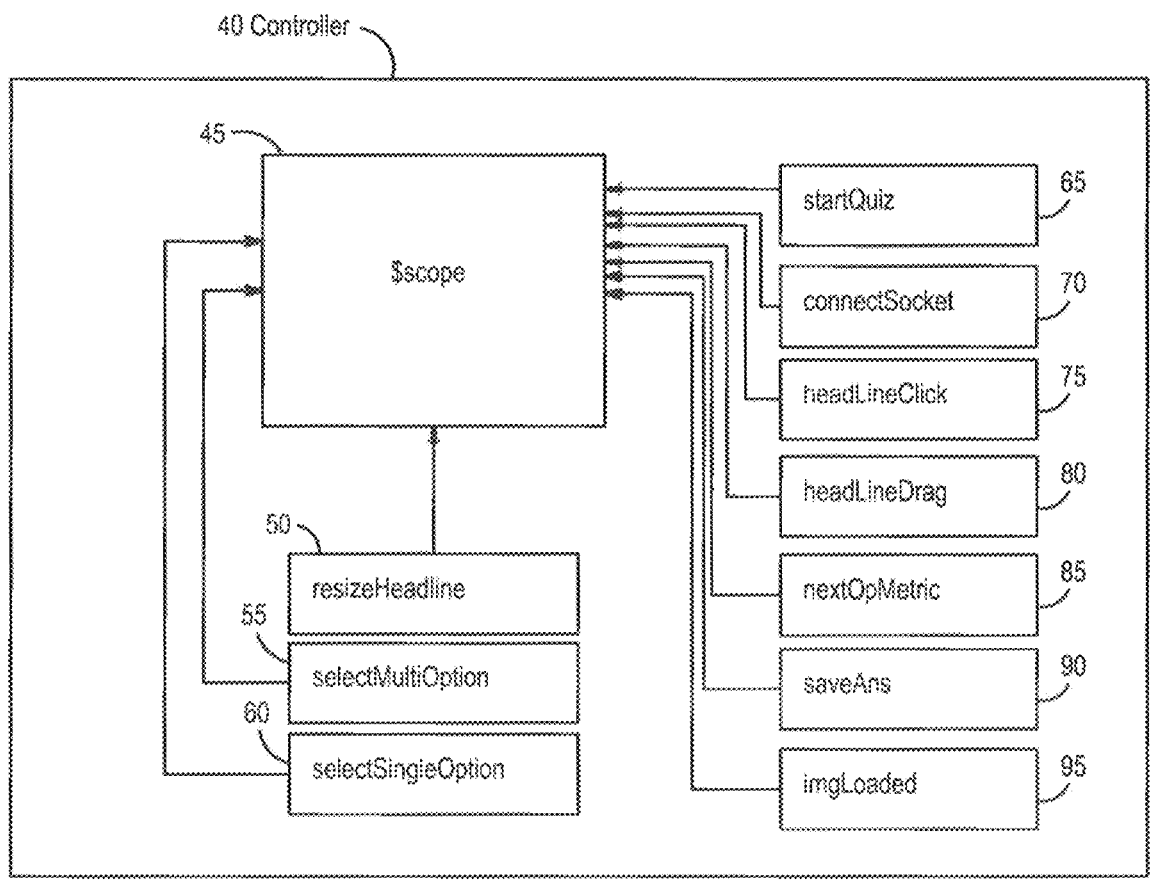
FIGS. 3a and 3b each comprise a schematic functional diagram showing certain functional aspects of a controller according to the FIG. 2 embodiment.
Figure 3B:
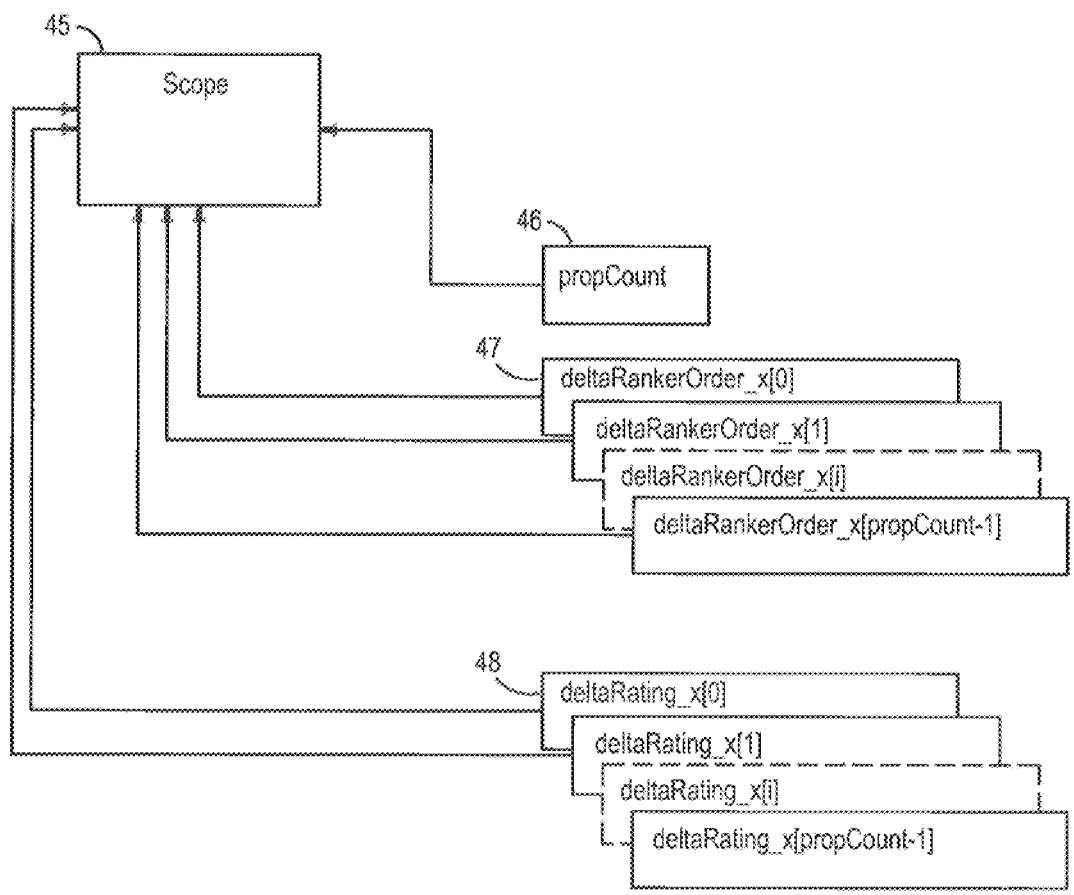

The detailed illustration in FIGS. 3a and 3b show the functional additions to the $scope object 45 (FIG. 2) made by the Controller 40. In FIG. 3a:

(i) startQuiz( ) 65: Called after the page loading finishes. This function calls connectSocket( ) 70, takes parameters associated with the deep-linked URL as described above, and passes them to startQuiz( ) function 13 (FIG. 2) of the WebServices object 12. The returned value displayed to the user is the first proposition in the first series of propositions (e.g., questions), as defined in (v) below, corresponding the first part of the survey. The use of term "display" in this context, and throughout the remainder of the present disclosure, refers to the functionality of the "View" component 30 of the MVC architecture.

(ii) connectSocket( ) 70: Establishes socket connection with the Server 16.

(iii) headLineClick( ) 75: Called when the respondent clicks on the scale displayed on the screen to rate an option. The notion of an infinite number of points on the scale, which would be valid if the survey was conducted on paper, is approximated in this Web-based system by associating the rating with the pixel at which the click is positioned. This function then passes the respondent's rating, computed in terms of the number of pixels along the scale, to saveAns function 15 of the WebServices object 12, and displays the next proposition in the current series of propositions, as defined in (v) below, which constitute the current part of the survey.

Figure 4A:
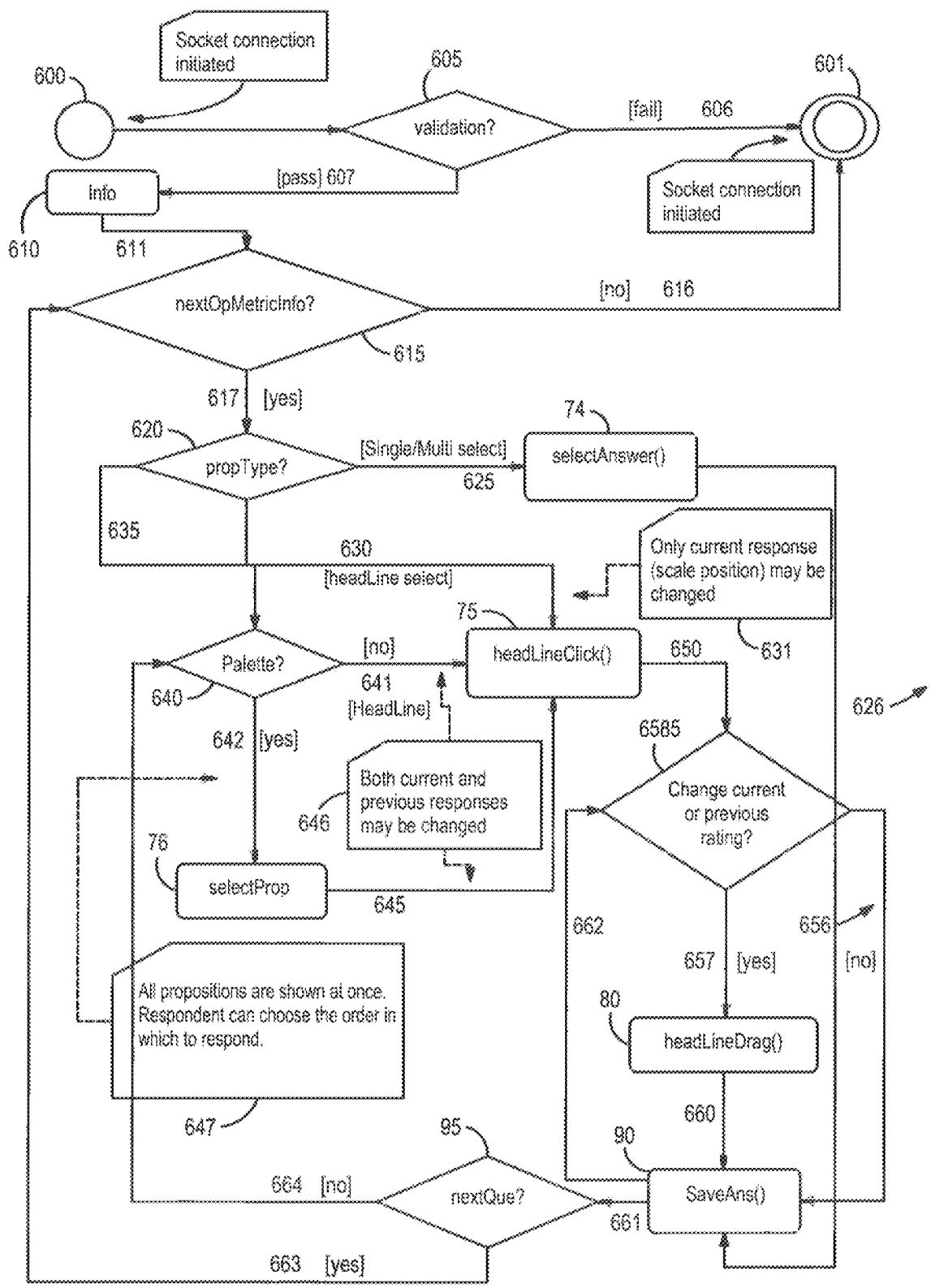
FIGS. 4a and 4b each comprise a flowchart showing certain functional steps according to the FIG. 1 embodiment.
Figure 4B:
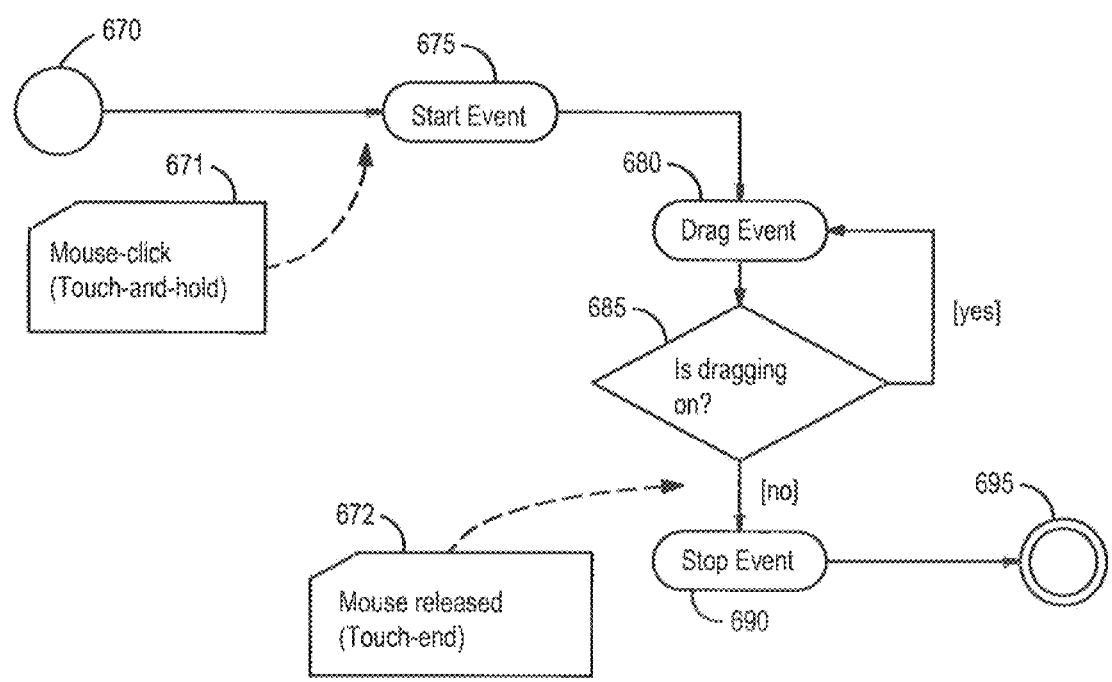

(iv) headLineDrag( ) 80: Called when the respondent wants to change the current and/or any one of the previous responses. It is noteworthy that the implementation of this function in the present embodiments preferably avoids using features now supported in HTML5, which could provide "drag-and-drop" functionality, but may result in substantial Web communications overhead. The Angular.js implementation in the present embodiments ensures that this functionality executes entirely on the client side. FIG. 4b provides a logic diagram for this functionality. When a "touch-and-hold" mouse click is detected, the function determines whether the mouse position touches the vertical bar connecting a label or image to the scale. The significance of the labels or images is explained below. The manner in which labels or images are connected to the scale can be visualized in the screen shots shown FIGS. 8-10. If the function determines that the click has occurred on a vertical connector at 671, start event 675, shown in FIG. 4b is generated which begins the "dragging." (See headLineDrag( ) function 80 in FIG. 4a). Subsequently, a timer-driven drag event 680 is generated, the processing for which determines the degree of movement along the scale and updates the View on the screen of GUI via steps 685 and 680. Finally, when the mouse button is released at 672, the stop event 690 is generated which terminates the drag operation and stores the final scale position in the database at 695. The Javascript source code for headLineDrag( ) 80 is provided in Appendix A. It should be noted that much of the functionality described above is provided by library functions from the JQuery development framework which are configured from an external HTML file when the application is loaded in the client's browser.

(v) nextOpMetricInfo( ) 85: The HTML encoding of the SPA (Single Page Application) includes a button which is rendered as the image >>on the page, as illustrated in the screen shots in FIG. 6-10. As described below, each part of the survey comprises a series of "propositions", the definition for which (accompanied by examples) is provided below. When the user clicks on this button and all of the propositions of the current part of the survey have been presented on the Web page and ranked by the respondent, this invokes the function nextOpMetricInfo( ) which triggers the retrieval of the next series of propositions, i.e. the next part of the survey, by invoking function 14 of the WebServices object 12. The returned value displayed to the user is the first proposition in the next series of propositions retrieved by the function 14. Alternatively, if not all of the proposition of the current series of propositions have been presented to the respondent, the next proposition in the series of propositions is presented. In FIGS. 6-10, the color palette bars in the upper left portions of those drawings are, from left to right: blue gray: white: burnt umber; white: amber; white; burnt umber; white; blue gray; white; burnt orange: white; blue gray: white; burnt umber; white; amber; white; burnt umber; white; blue gray; white; and burnt orange. The horizontal scale bars are burnt orange.

(vi) saveAns( ) 90: Forwards the data passed as an argument to the saveAns function 15 of the WebServices object 12. In FIG. 4a, the execution path of this function may be traced starting from nextOpMetricInfo( ) function 85, and going through selectAnswer( ) function 74, headLineDrag( ) function 80 and/or headLineClick( ) function 75, and in all cases the returned value to the user does not alter the Web page display. By invoking this function through each of the aforementioned paths of execution, the system is able to accumulate multiple ratings for any given proposition, all of which may be discarded during the post-processing of the data. However, as a means of minimizing network communications overhead, the Controller 40 may be configured in order to circumvent all of these execution paths, in which case this function is invoked only when nextOpMetricInfo( ) function 85 invokes Webservice function 14 to proceed to the next series of propositions in the survey.

On the other hand, if multiple ratings are accumulated prior to invocation of nextOpMetricInfo( ) the variation in such ratings becomes the basis for psychometric measurements not previously captured by existing opinion surveying methodologies. These measurements are based (preferably only) on those ratings recorded by saveAns( ) function 90, once all the propositions have been presented to the respondent. As shown in FIG. 3b, the Scope object maintains a counter of the number of propositions already presented, which can be compared to the number expected according to the property noProps 160 of the OpinionMetric 100 data structure, both of which are described below. As such the Controller 40 may determine whether all propositions are present, so that this is flagged in the data recorded by saveAns(( ) function 90. If the propositions are presented sequentially, then on leaving the decision block 640 (FIG. 4a), the execution path is 641. Alternatively, if the execution path is 642 on leaving the decision block 640, the proposition is selected from a Palette in selectProp( ) function 76 before invoking the headLineClick( ) function 75 via execution path 645. In either case, with each successive execution of headLineClick( ) function 75, the attribute Scope.propCount 46, shown in FIG. 3a, is incremented. When the attribute Scope.propCount 46 is equal to the value of the property noProps 160, shown in FIG. 5b, SaveAns( ) function 90 is invoked with the appropriate flag to indicate that all propositions are present. FIG. 3b also illustrates the objects 47 and 48, in which the accumulated values of the variation in rank order or ratings for individual subjects can be cached, the application of which is described below.

(vii) imgLoaded( ) 95: This function is called by a "Directive" called "imageonload", built into the Angular.js framework, which triggers a call to resizeHeadLine 50 ( )

(viii) selectSingleOption( ) 60: Called when propType, (defined below) is Select (single)

(ix) selectMultiOption( ) 55: Called when propType is Select (multiple).

(x) resizeHeadLine( ) 50: Optimizes visual display of the scale.

FIGS. 4a and 4b depict the process flow of an Opinion Survey produced by the factory of the preferred embodiment.

Once the initial HTML code with embedded Angular.js code is loaded in the browser (client side), the Web socket manager 600 initiates a request to connect with the Server 16 (FIGS. 2-16 Server NodeJS). If the credentials of the Web client are validated 607 in the decision block 605, the process 610 delivers an introductory page to the Web client browser, which page includes an explanation for proceeding through the survey. Alternatively, if the credentials do not pass validation 605, the socket connection request is aborted at 606, and the connection is closed at 601.

The steps in this paragraph describe the algorithmic process flow following invocation of nextOpMetricInfo( ) function 85. With reference to FIG. 4a, the survey begins when this function is invoked as described above. The decision block 615 processes the response from the server-side function nextOpMetric 18. If there is an additional series of propositions to be presented at 617, the execution path is determined by the decision block 620, based on the value of propType, discussed below: if not, path 616 leads to closing the socket at 601. There are three possible paths emanating from decision block 620. Path 625 is executed when the value of prop Type is "Single/Multi select", which is answered at 74 using the standard HTML input selection mechanisms of check boxes (multiple select) or radio buttons (single select). The second and third paths result in the use of the scale described above, and labeled as "headLine" in FIG. 3. Path 630 corresponds to a value of "headLineSelect" for propType, in which case the rating on the scale may only be modified if the respondent has not yet proceeded to the next proposition, as explained in descriptor 631.

Path 635 corresponds to either a value of headLinePalette" or not. In the case of "headLinePalette", the decision block 640 follows the execution path 642 and, as described below, the function 76 enables selection of the proposition from the "palette" which offers a simultaneous display of the entire series of propositions. The execution path 645 then proceeds to headLineClick( ). function 75. If the decision block 640 determines that the prop Type is "headLine" (i.e. there is no "palette"), the execution path 641 is followed directly to headLineClick( ). function 75 As indicated in the descriptor 646, when the headLineClick( ) function 75 is reached via execution paths 641 or 645, the ability to change either the current or previous responses is retained.

headLineClick( ). function 75 leads over path 650 to the decision block 655 which allows the respondent to change responses (i.e. ratings on the scale). If the prop Type was "headLineSelect", this functionality is allowed only for the current response 631, whereas the prop Type values "headLine Palette" and "headLine" enable changes to previous responses 646. In either case, the path 657 to headLineDrag( ) function 80 enables the respondent to change a rating using the "drag-and-drop" functionality described below.

On exiting headLineDrag( ) function 80 via path 660, saveAns( ) function 90 is invoked, which operates as described in (vi) above. Likewise, if the answer in decision block 655 is no, path 656 proceeds to saveAns( ) function 90. Further, after the answer is selected at 74, path 626 also leads to saveAns( ) function 90. On exiting saveAns( ) function 90, there are two possible execution paths, depending on the user input selection. When the user clicks on the button rendered as ">>", the execution path 661 leads to the decision block nextQue 95. If all of the propositions in the current series have been presented, nextOpMetricInfo( ) function 85 is invoked via the execution path 663. Otherwise the next proposition in the series is presented on the screen and the execution path 664 returns to function 75 headLineClick( ).

Where all propositions are shown at once, the descriptor 647 indicates that the user may choose, in selectProp( ) function 76, the order in which to select from the Palette 640, before following execution path 645 to headLineClick( ) function 75. Timestamps may be used for each rating (i.e. each time user clicks on the scale) in order to measure duration associated with each rating (i.e. how much time the user took to make an individual selection on the scale).

Preferably, the data recorded by saveAns( ) function 90 includes the headline rating accompanied by timestamps for the entries into headLineClick( ) function 75 and saveAns( ) function 90. These timestamps enable the duration of each rating to be captured, from the time a subject label is selected, until it is dropped somewhere on the scale and the mouse or user input device is released.

In post-processing of the accumulated ratings for the set of P(x) in a given opinionMetric, the fluctuation in ratings and rank ordering for a given subject x is preferably measured as the total "delta", or the accumulated difference in value between each successive rating. Suppose for example, that there are three changes to the rank ordering of a set of four (4) subjects x, and that the initial rank order of subject x1 is fourth position and that its subsequent rank orders are first, third, and second. This represents a total delta in the value of the ranking for x1, before the respondent advances to the next set of propositions, equal to 6 (4−1=3, 3−1=2 and 3−2=1). Furthermore, the amount of time taken for each successive iteration through the execution path from headLineClick( ) function 75 to saveAns( ) function 90, may have additional psychometric value to be applied in the post-processing. This is context-dependent in that, in some instances, a longer duration for each change in rating may be interpreted as having relatively more weight whereas in other cases, it would have relatively less weight.

The interpretation of the measurements is context-dependent. Potential use cases are described in the sections below.

In one exemplary embodiment, the features of a new product are compared to a series of existing products. When all the existing products have been presented to the respondent, the rank ordering recorded by SaveAns( ) has established the preferred brand. At this point, the introduction of a new product feature may be disruptive to the rank ordering of the existing products for that feature. In particular, it may result in the preferred brand losing its rank as preferred even with respect to the existing products. The extent to which respondents change ratings or rank ordering, prior to the invocation of nextOpMetricInfo( ) may be interpreted as a measure of "brand loyalty".

In another exemplary embodiment, the variation in ratings of an attribute of these products may be used to establish a metric that is representative of "rigidity", which can be defined as the degree of certainty in evaluating this attribute for the specific brand. If the rank order of an attribute for a specific brand fluctuates significantly, prior to invocation of nextOpMetricInfo( ), the level of certainty of the respondent with respect to the evaluation of the feature may be said to be low.

In yet another exemplary embodiment, variation in rank ordering or ratings, prior to invoking nextOpMetricInfo( ), may also be interpreted as a measure of "open-mindedness". It is anticipated that this metric may be applicable in political opinion polling. For instance, in a survey of preferences for the positions of various political parties on policy issues, wide variations in rank ordering may be interpreted as reflecting an absence of ideological adherence. Suppose that the propositional predicate is the position of a party with respect to multi-culturalism, and that a respondent starts by assigning the highest ranking to a party associated with anti-globalist sentiment. If that ranking is substantially changed before invoking nextOpMetricInfo( ), it becomes conceivable to interpret the change as attributable to the fact that the respondent does not subscribe to an entrenched view, and therefore to characterize this as "open-mindedness". But it is also conceivable that this may simply reflect a lack of awareness of, or interest in, the issue. It will always remain the choice of the survey designers and analysts as to whether to use the post-processed results as a metric for "open-mindedness", and this choice will, in most instances, depend on factors such as the type of subjects in the propositional functions, and the demographic characteristics that may be known about the respondents in terms of age, location, income and so on.

As illustrated in FIG. 5, an important object produced by the factory is the "opinionMetric." This is defined as an irreducible component of a Web-based Opinion Survey in that it encompasses the body of information which the factory presents to, and elicits from, a respondent (i.e. a Web client) in the context of one of the eight (8) use cases identified above.

An opinionMetric object is served to a Web client processor in a Javascript Object Notation (JSON)-encoded message. This is sent from at least one server-side processor in response to the invocation of the function nextOpMetricInfo. The core properties of an opinionMetric are preferably defined using the paradigm of propositional logic. A propositional function, expressed as P(x), contains a "predicate" P and a variable subject x. The propositional function or simply "proposition," expresses a question to which the respondent's answer corresponds to the evaluation of this function. For example, when the predicate "How do you feel about the trustworthiness of . . . ? " is applied to the subject "dogs", the proposition is "How do you feel about the trustworthiness of dogs?". If applied to the subject "people", the proposition becomes "How do you feel the about trustworthiness of people?". The answer to these questions constitutes the evaluation of the propositional functions P(x), for the set of x={"dogs", "people"}, and the aggregate of the answers from a plurality of respondents becomes the basis for establishing the "metric" targeted by the opinionMetric.

Figure 5A:
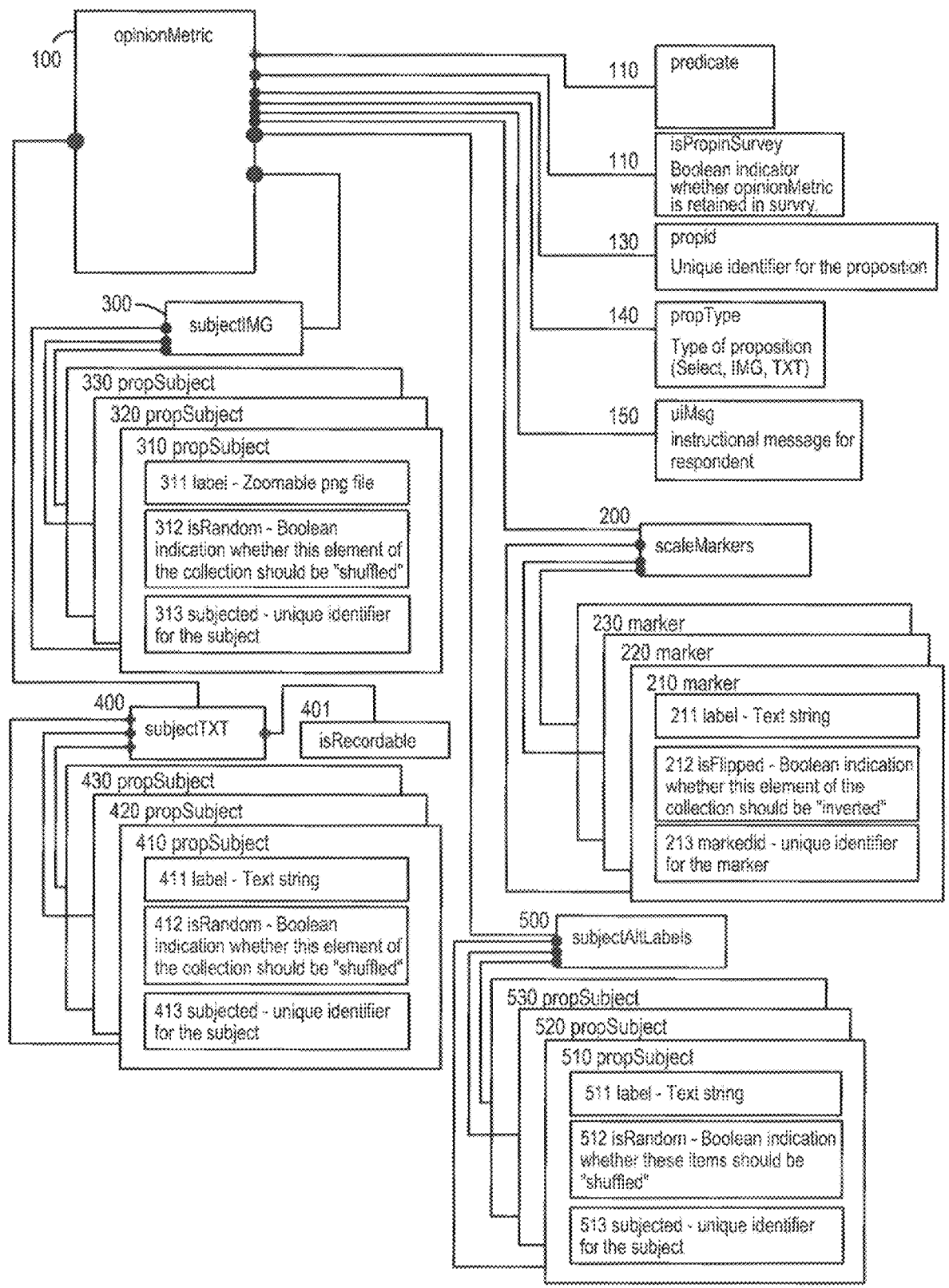
FIGS. 5a and 5b are schematic functional diagrams showing a preferred opinion metric data structure according to the FIG. 1 embodiment.
Figure 5B:
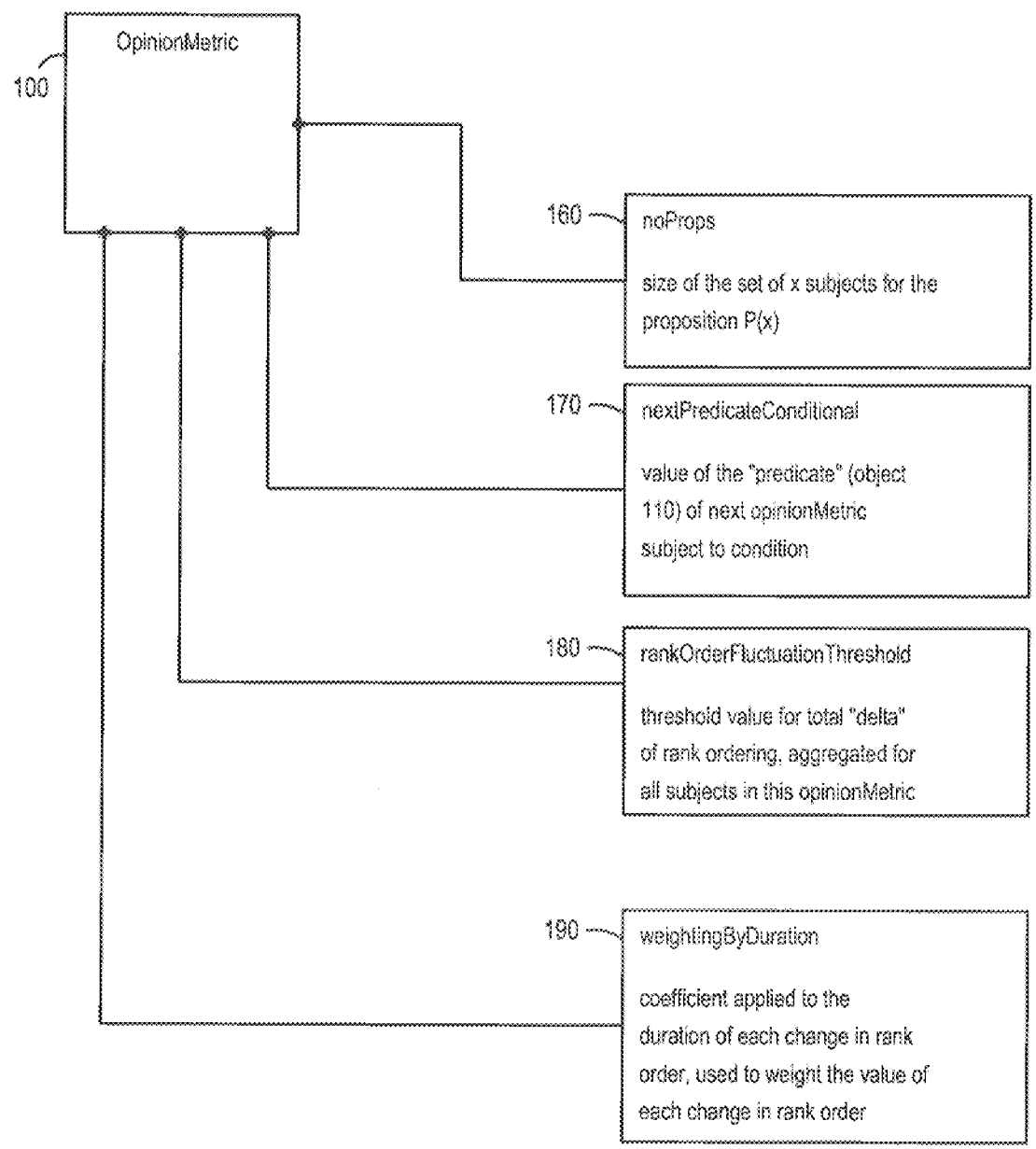

FIGS. 5a and 5b illustrate that the opinionMetric object 100 preferably has the following properties:

(i) Object 110 is the predicate P of a propositional function P(x), in the form of a text string.

(ii) Object 120 is a Boolean value indicating whether the Opinion Survey process should skip this opinionMetric and retrieve the next one from the server-side.

(iii) Object 130 is a unique identifier for the proposition.

(iv) Object 140 preferably defines the type of proposition (propType), which is essentially the User Interface format of the proposition. There are three basic formats offered by the factory, all of which use a text string for the predicate: (a) image-based (IMG)—where the subject x of P(x) is presented using an image; (b) where the subject is a text string: (c) where the subject is a standard selection box (e.g. check box or radio button).

(v) Object 150 is an optional message providing the respondent with any additional instructions required to respond to the specific propositions for this opinionMetric.

(vi) Object 160, illustrated in FIG. 5b, indicates the number of propositions P(x), which is equivalent to the size of the set of subjects represented by x.

(vii) Object 170, illustrated in FIG. 5ba, is preferably the value of the predicate (object 110) of the next opinionMetric to be presented conditionally to the respondent. When a pre-defined condition is met, the Web Server nextOpMetric function 19 searches the questionnaire for the opinionMetric of which the predicate equals the value of nextPredicateConditional (object 170). This mechanism supports the ability to design the questionnaire such that it can branch off from the default sequence in which the opinionMetric objects are presented, based on the results obtained so far.

(viii) Objects 180 and 190, illustrated in FIG. 5-a, are the parameters of an exemplary embodiment of the aforementioned mechanism for changing the questionnaire sequence based on the evaluation of a pre-defined condition. In this instance, the condition is defined in terms of the aggregate total "delta" for rank ordering of subjects, computed based on the values cached in object 47 and shown in FIG. 3b as part of the Scope object. The threshold may be defined either as a maximum or a minimum, so that the condition is triggered when the total "delta" either exceeds it or falls below. Object 190 is the value of a coefficient that may be applied to each change in rank order, where the duration, as captured by the timestamps for entering headLineClick( ) function 75 and saveAns( ) function 90, is preferably used to weight the change in value. Alternative embodiments of this condition may use the total delta for ratings, illustrated as object 48 in FIG. 3b. Furthermore, the condition may be defined in terms of total "delta" for any of the individual subjects in the opinionMetric, rather than the aggregate values for the entire set of subjects.

The remaining properties of the opinionMetric (objects 200-500) contain collections of data structures requiring further detailed explanation which follows.

Object 200 preferably contains a collection of "scaleMarkers" 210, 220, 230, etc. Since the rating scale is non-numerical, these markers are used as guideposts to indicate to the respondent the relative level of agreement with (or preference for) the proposition. Each marker in the collection preferably has the following properties:

(i) Label 211: a text string representing the level of agreement with, or preference for, the proposition.

(ii) isFlipped 212: a Boolean value indicating whether the markers should be displayed such that increasing agreement is left-to-right or vice versa.

(iii) markerId 213: preferably the unique identifier for the marker.

Object 300 preferably contains a collection of propositional subjects ("propSubjects") 310, 320, 330, etc., corresponding to the case where the value of propType 140 is IMG. These are for image-based subject presentation. Each propSubject in the collection preferably has the following properties:

(i) label 311: a zoomable .PNG (Portable Network Graphics) file providing an image that conveys the subject x in P(x). Examples of this may refer to a product or service concept, feature, brand or any other propositional subject that lends itself to visual representation.

(ii) isRandom 312: a Boolean value indicating whether the propSubject in this collection should be shuffled (randomized) before presentation to the respondent.

(iii) subjectId 313: unique identifier for the subject.

Object 400 preferably contains a collection of propositional subjects 410, 420, 430, etc., corresponding to the case where the value of propType 140 is TXT. These are for text strings for subject presentation. Each propSubject in the collection preferably has the following properties:

(i) label 411: a text string identifying the subject.

(ii) isRandom 412: a Boolean value indicating whether the propSubjects in this collection should be shuffled (randomized) before presentation to the respondent.

(iii) subjectId 413: preferably the unique identifier for the subject.

Object 400 preferably also contains the Boolean variable 401 (isReorderable) indicating whether the propSubjects in the collection can be re-sequenced by the Server prior to sending the entire opinionMetric to the Web client.

Object 500 preferably contains a collection 510, 520, 530, etc., of alternative "labels", which are text strings for subjects corresponding to the case where the value of propType 140 is TXT. Each propSubject in the collection preferably has the following properties:

(i) label 511: the alternative text string.
(ii) isRandom 512: a Boolean value indicating whether the propSubjects in this collection should be shuffled (randomized) before presentation to the respondent.
(iii) subjectId 513: unique identifier for the subject.

Figure 6:
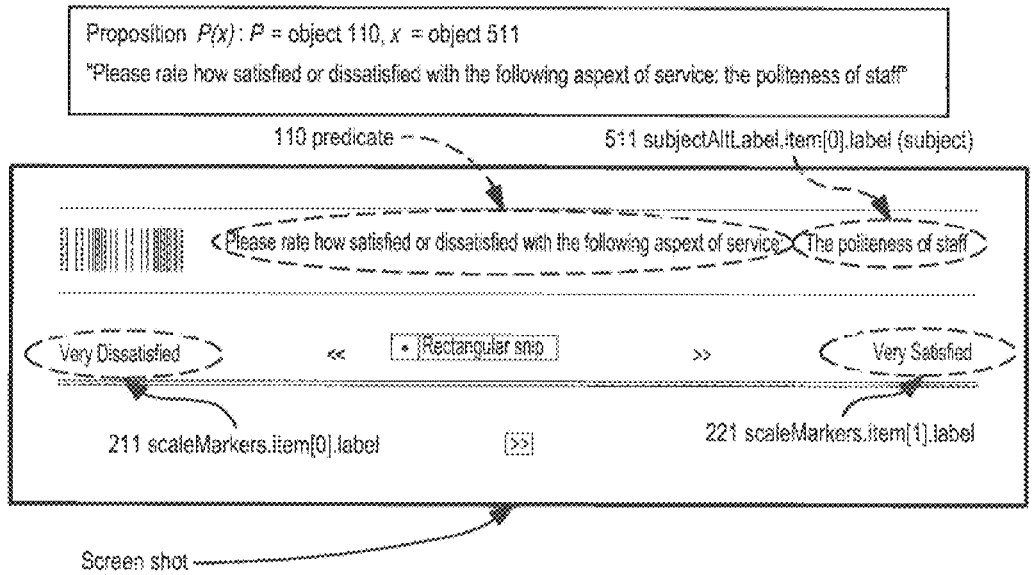
FIG. 6 is an initial proposition GUI screen shot according to the FIG. 1 embodiment.

The screen shot incorporated in FIG. 6 provides an example of how the following objects appear on the Web page when the opinionMetric data is received by the client-side processor and the proposition (propType 140=TXT) for the first subject is introduced to the respondent:
(i) predicate 110
(ii) object 511, the "label" property of the first propSubjects in the collection belonging to subjectAltLabels 500.
(iii) objects 211 and 221, the "label" properties of the first and second markers in the collection belonging to scale-Markers 200. The user clicks anywhere on the scale to indicate, in this instance, the level of satisfaction with the politeness of staff.

FIG. 6 corresponds to a "Customer Satisfaction" opinion-Metric for a specific service already identified to the respondent in the introductory page (not shown). The concatenation of Predicate 110 ("Please rate how satisfied or dissatisfied with the following aspect of service:") with label 511 ("The politeness of staff") forms the "proposition" for the first is this series of propSubjects, and is displayed to the respondent as the string "Please rate how satisfied or dissatisfied with the following aspect of service: The politeness of staff".

Figure 7:
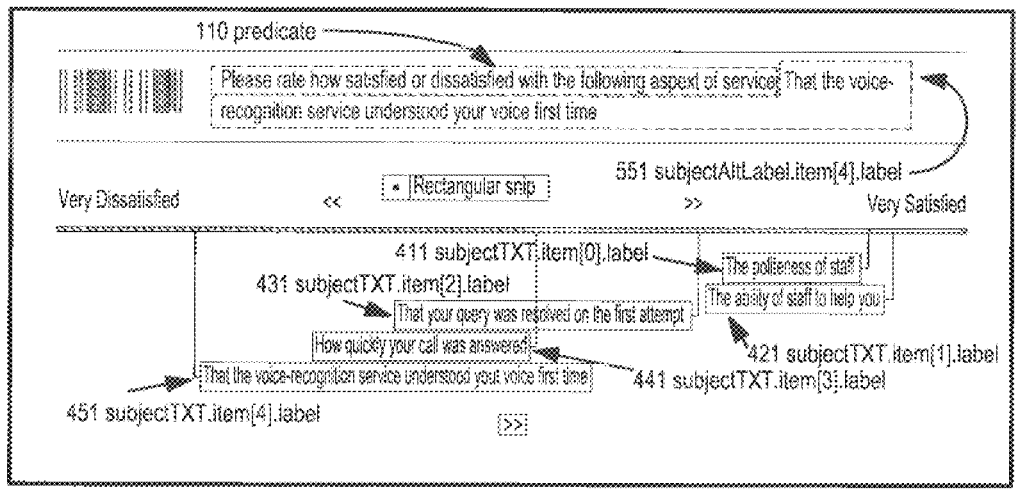
FIG. 7 is a final proposition GUI screen shot according to the FIG. 1 embodiment.

In this example, the "Customer Satisfaction" opinionMetric uses subjectTXT 400. FIG. 7 incorporates a screen shot of the same Web page, updated to show that all the subjectProps in the collection belonging to subjectTXT 400 have been introduced to, and rated by, the respondent. The values of subjectTXT.subjectProp[i].label (for i=0,1,2,3,4) are displayed below the scale at the positions where they have been rated by the respondent. The proposition displayed above the scale—"Please rate how satisfied or dissatisfied with the following aspect of service: the politeness of staff: That the voice recognition service understood your voice first time". incorporates the last element (object 551) in the collection of subjectProps belonging to subjectAltLabel. This string is also the property of the last subjectProp (object 451) in the collection belonging to subjectTXT (object 451). Therefore this string ("That the voice recognition service understood your voice first time") appears below the scale with reference to the proposition to which the respondent indicated the least satisfaction.

It should be noted that the sequence of introduction of the subjects may be different from the order in which they are sent from the server if the value of "inRandom" is TRUE, since this would trigger a randomized shuffling of the subjectProps collection before they are introduced to the respondent.

The mechanism enabling the respondent to re-assess any of the subjects of a proposition is illustrated in FIGS. 8*a* to 8*e*. The proposition is that the respondent may find some degree of appeal to the inclusion of various substances in chocolate. Each of a plurality of substances in presented to the respondent as an alternative subject of the proposition. Where the respondent clicks on the rating scale, the subject is locked onto the corresponding position.

Figure 8A:
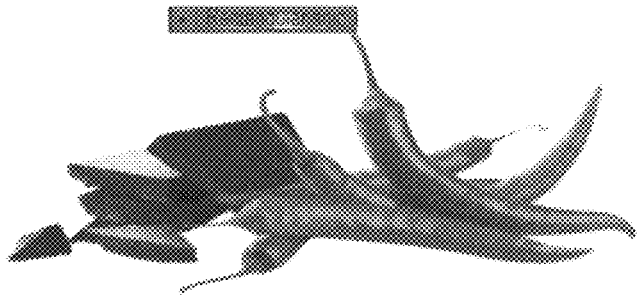
FIGS. 8a, 8b, 8c, 8d, and 8e are GUI screen shots showing drag and drop processes according to the FIG. 1 embodiment.
Figure 8B:
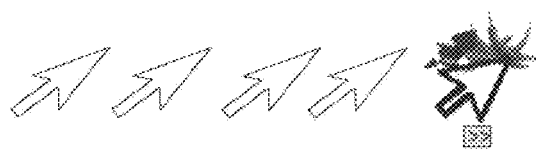

However, this is only a tentative rating of the subject as the respondent has the option of changing the rating at any time until the survey has advanced to the next proposition. This is illustrated in FIGS. 8*a* and 8*b*. FIG. 8*a* shows that the respondent has rated the concept of putting chili into chocolate as very unappealing. However, as shown in FIG. 8*b*, the respondent may change the rating using the function 80 headLineDrag( ), described above. By clicking on the label of the subject, the respondent may unlock the subject, slide it anywhere on the scale while holding the mouse button, and lock it into a new position by releasing the mouse button. In this instance, it is impossible to determine whether the decision to re-rate this concept as mildly appealing is a momentary aberration or reflects a legitimately eccentric taste on the part of the respondent.

Figure 8C:
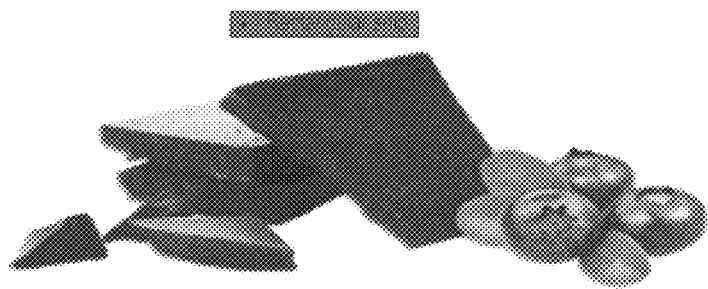
Figure 8D:
Figure 8D:
Figure 8D:
Figure 8D:
Figure 8E:
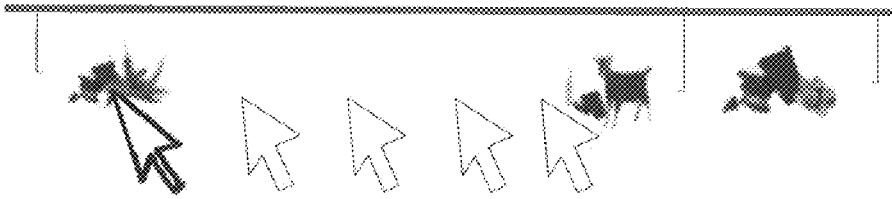
Figure 8E:

But this kind of uncertainty is mitigated once a plurality of subjects have already been rated, since an individual rating can be re-assessed in terms of the relative rankings of all the subjects. In FIG. 8*c*, the concept of chocolates containing blueberries is introduced and the respondent rates this closer to the "Very Appealing" upper end of the scale. Then, in FIG. 8*d*, the concept of chocolates made from goat's milk is introduced, which the respondent is willing to consider as mildly appealing. Since the rating immediately exposes the rankings relative to the other concepts already rated, the respondent is induced to rate goat's milk chocolate in terms of whether it is preferable to "chocolate with chili." But then rating goat's milk chocolate with this method brings back into focus the respondent's uncertain cognitive process which led to the rating of "chocolate with chili" as mildly appealing. At this point, the respondent has the option to revisit that process and to decide whether the rating was an aberration or an accurate reflection of eccentric taste. FIG. 8*e* illustrates the case where the re-assessment results in the conclusion that the prior rating of "chocolate with chili" was an aberration and where the respondent uses the headLineDrag function of Controller 40 to re-rate the concept.

Figure 9:
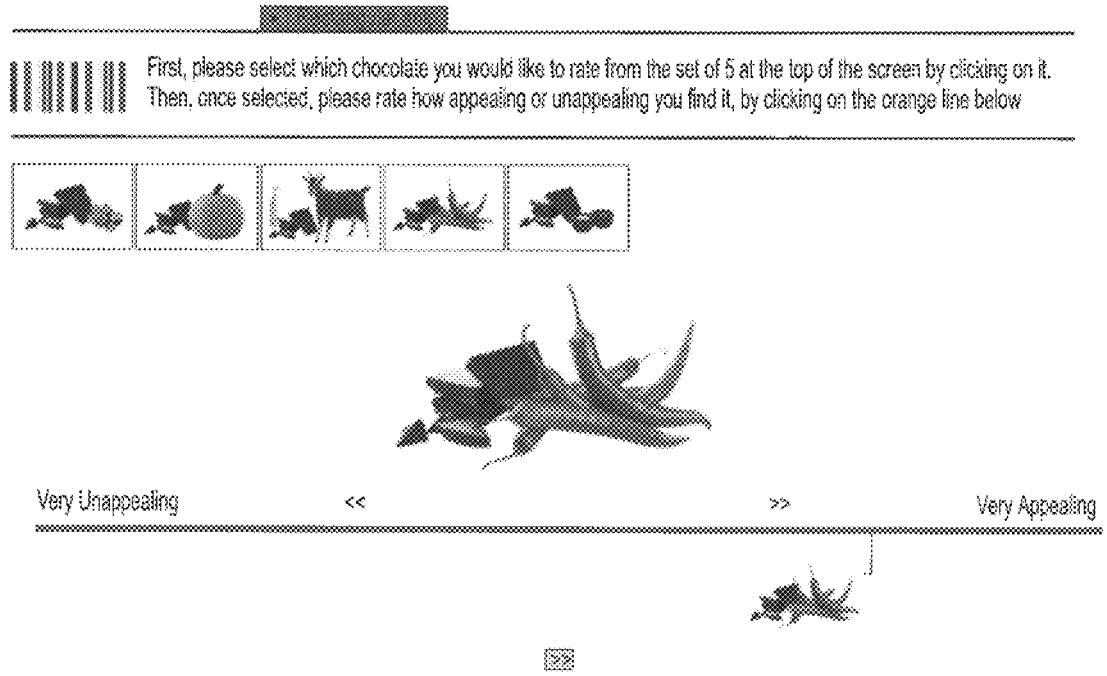
FIG. 9 is a selection screen shot according to the FIG. 1 embodiment.
Figure 10:
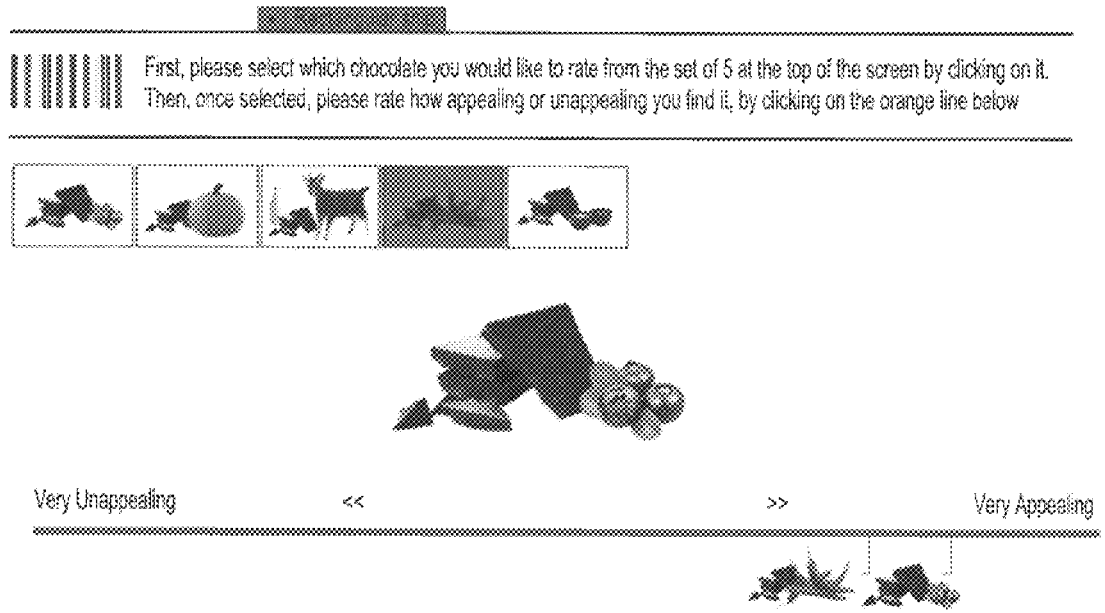
FIG. 10 is another selection screen shot according to the FIG. 1 embodiment.

Order bias may be even further reduced by circumventing the sequential presentation of the subjects. This is accomplished as shown in FIGS. 9 and 10. In FIG. 9, all of the subjects proposed as potentially appealing when included in chocolate, as described above, are presented simultaneously in a section at the top of the page which is defined as a "palette." The instructions provided in uiMsg 150 explain to the respondent to first highlight any of the subjects by clicking on the corresponding image in the palette and then to rate the level of appeal by clicking on the scale below. In an alternative instantiation of this functionality, the respondent may "drag-and-drop" the image, corresponding to the selected subject, directly from the palette onto the scale. FIG. 10 illustrates that once the first subject is selected (chocolate with chili) and its rating indicated on the scale, the corresponding image i.e. the subjectIMG.propSubject[i] .label object, is showed as "disabled" to indicate that it has been removed from the available options and its underlying HTML-encoded attribute is changed to prevent a duplication of its selection. FIG. 10 also depicts the selection of the next choice from the palette (chocolate with blueberries), and its rating on the scale such that it is rank-ordered in preference to the first selection of chocolate with chili.

Conjoint.

As previously described, conventional rating scales based on a restricted set of discrete values result in a loss of information, which is avoidable using the pixel density of the scale (along which respondents rate products, services, features, etc.) to define increased granularity of the ratings. This becomes applicable in conjoint analysis of survey data comprising ratings of combinations of features, where some features do not have quantifiable attributes. To illustrate an example, suppose there is a set of three features to be considered for marketing of a new drug, consisting of price, onset of action (time required to take effect), and side effects.

A survey would be designed to acquire ratings of different combinations of these features ("profiles"), as inputs to a conjoint analysis. In the context of statistical regression used in conjoint analysis, the ratings of the profiles are measures of the dependent variable while the three features constitute the independent variables, or "predictors". The first two, price and onset of action, can be represented by integer variables and are therefore measurable along numeric scales. However "side effects" is a qualitative attribute, with possible values such as "nausea", "drowsiness" and "loss of appetite", all of which could potentially be part of a particular rated profile, and since they are not defined numerically, do not lend themselves to statistical regression techniques. However, if they are rated in terms of a linear scale of tolerance, the resulting ratings provide a means of quantifying the predictor variables in the regression analysis performed on the survey data.

Figure 11A:
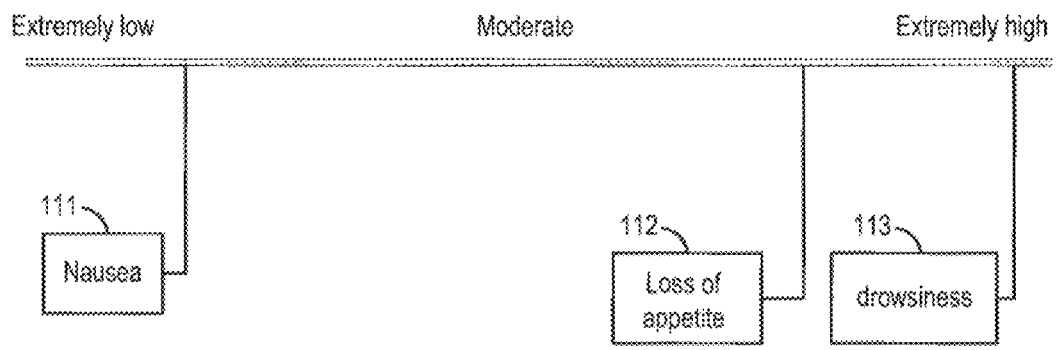
FIGS. 11a and 11b are schematic diagrams showing a tolerance scale for drug side effects, and preference ratings for a drug choice set, according to an embodiment of the present invention.

This is illustrated in FIG. 11a, where a respondent uses the scale to assign quantitative measures to drowsiness 111, loss of appetite 112, and nausea 113 in terms of the respondent's personal capacity for tolerance of these conditions. These ratings can then be used to assign numerical values to the "side effects" feature in each of a set of profiles presented to the respondent for rating along a preference scale.

Figure 11B:
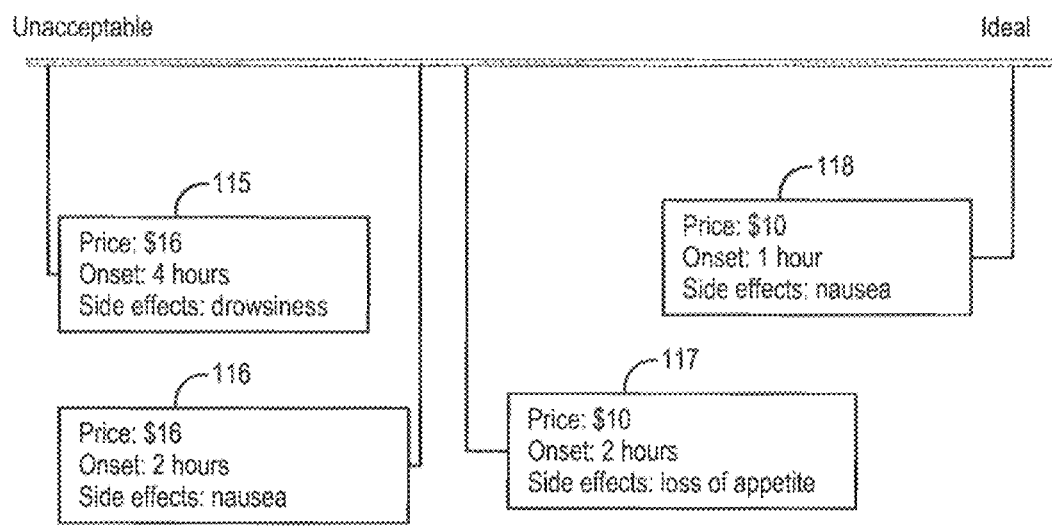

As shown in FIG. 11b, the ratings could indicate that preference is more sensitive to changes in "onset of action" than any other feature, to the extent that a profile with "nausea" (the side effect to which the respondent has already indicated extremely low tolerance) is nevertheless preferable to other profiles with side effects for which there is greater tolerance, because the "onset of action" value is the lowest. The profiles presented to, and then rated by, the respondent, are the result of a "choice set design". For example, the respondent may rate (at 115) as "Unacceptable" a drug which costs $16.00, has a onset of four hours and a drowsiness side effect at 115. Slightly more preferable may be a selection (at 116) where a drug costs $16.00 but an onset of two hours and a side effect of nausea. Even more ideal may be a choice of drug (at 117) that costs $10.00, has an onset of two hours and a side effect of loss-of-appetite. An ideal choice (at 118) for this respondent may be a drug costing $10 and a side effect of nausea, but with an onset of only one hour.

In FIGS. 11a and 11b, since all of the features are numerically measured, multiple regression analysis of the preference ratings can then be applied to the task of designing a new choice set for presenting in a subsequent iteration the survey. Successive iterations of this process constitutes a novel approach to "adaptive" conjoint analysis.

Figure 12:
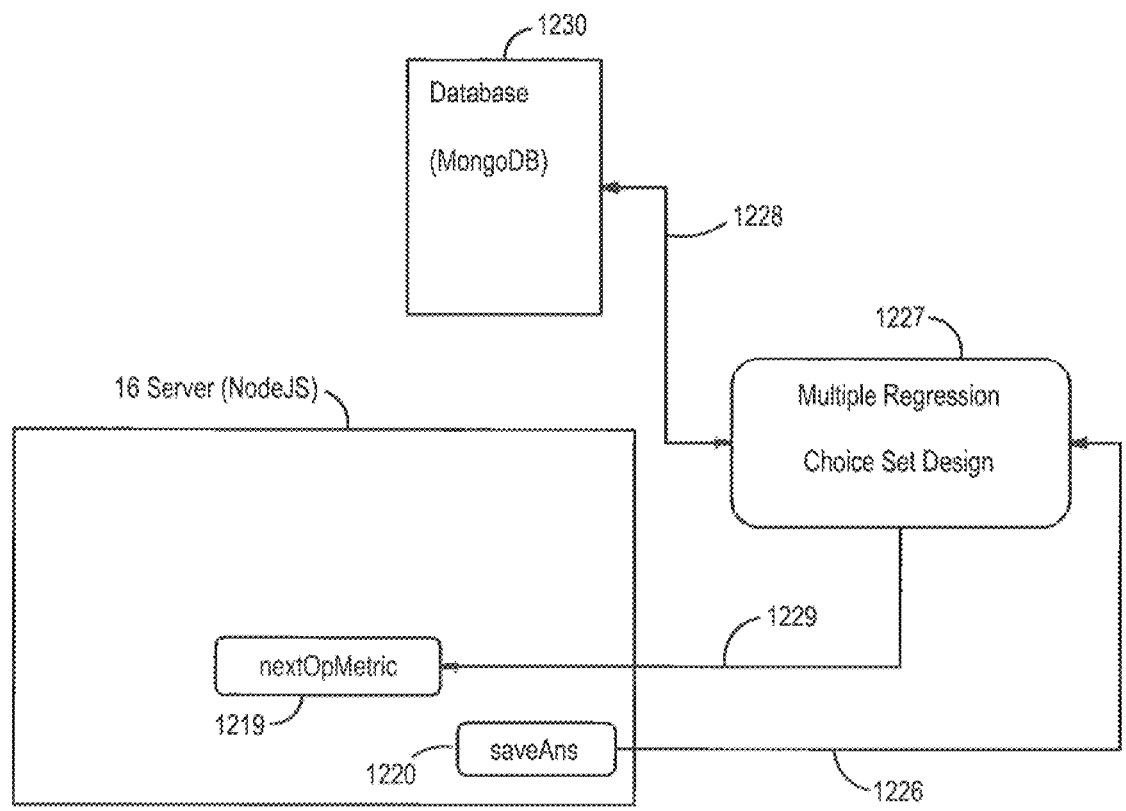
FIG. 12 is a functional block diagram illustrating how external functions interact with the service side components.

It should be noted that application of the present invention in the framework of adaptive conjoint analysis may, in some embodiments, use interaction between the server side of the MVC architecture illustrated in FIG. 2, and external functions comprising multiple regression techniques applied to the collected survey data and a choice set design algorithm for selecting the next set of profiles. FIG. 12 illustrates how these external functions interact with the service side components: (i) The server side saveAns( ) function 1220 sends notification 1226 to the process 1227; (ii) process 1227 encompasses multiple regression functionality and a "choice set design" algorithm; (iii) in 1228, data collected from respondents is retrieved from the database and processed as part of the multiple regression; (iv) the results of the multiple regression are fed into the choice set design algorithm which defines a new series of profiles for respondents to rate, which are identified in step 1229 to the nextOpMetric function 18 which propagates the selected profiles to the client side.

The individual components shown in outline or designated by blocks in the attached Drawings are all well-known in the electronic processing arts, and their specific construction and operation are not critical to the operation or best mode for carrying out the invention.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A Web-based opinion survey client device apparatus operable to cause a plurality of propositional function responses to be provided from the client device to at least one web-based survey server, the propositional functions expressed as P(x), where P and x are respectively the predicate and the subject of said P(x), where each said P(x) is evaluated in the at least one client device for a plurality of subjects, each with a different value of x, wherein said predicate and said plurality of subjects are pre-configurable on the at least one survey server, the client device comprising:

at least one client device display;
at least one client device input;
at least one memory storing program code which when executed constitutes a Web Single Page Application (SPA),
wherein the SPA does not interact with the survey server during execution, thereby obviating any client-server interaction that would engender network communications latency and adversely affect motivation of respondents to be thorough in completing the web-based opinion survey-; and
at least one processor executing said SPA to cause the client device to
perform at least one process for each said P(x), comprising:
to display on the at least one client device display the each P(x) plurality of subjects;
causing said SPA to display on the at least one client device display:
a non-numerical scale of which a measure of granularity is directly proportional to the number of pixels spanned by said scale,
wherein the non-numerical scale is displayed as a linear scale having a first end and a second end; and
for each P(x) plurality of subjects, causing the client device to display on the at least one client device display a plurality of pre-configurable labeled markers along said scale to provide an indication on said scale of a relative level of agreement with, or preference for, the proposition expressed by the corresponding P(x);
for each P(x) plurality of subjects, causing the client device to enable at least one client to express opinion on said scale using the at least one client device;
input, whereby a pixel position corresponding to the position of the client input selection comprises a rating for the selected subject; and
for each P(x) plurality of subjects, forwarding said ratings to the at least one survey server, wherein a page displayed on the client device concurrently displays a palette comprising a plurality of rating images adjacent said scale for each P(x) plurality of subjects, wherein the plurality of rating images are randomly reordered in the palette prior to their presentation to each client of the web-based opinion survey;

wherein said client device enables the client, for each of the plurality of rating images, to express an opinion by dragging and dropping each of the plurality of rating images from the palette onto the scale, whereby the pixel corresponding to a drop position comprises the rating for the rating image, and wherein the opinion for each of the plurality of rating images is changeable by dragging and dropping each of the plurality of rating images to a new drop position on said scale, wherein the ability to change the opinion mitigates a possibility of order bias.

2. The apparatus according to claim 1, wherein the scale is absent indicia of differing scale values.

3. The apparatus according to claim 1, wherein for any one of said plurality of P(x), the client device sends to the at least one survey server a plurality of survey evaluations performed on the client device, said plurality of evaluations, enabled by said SPA, obviating repetitive client-server interaction, thereby avoiding network latency.

4. The apparatus according to claim 1, wherein the client device receives the SPA from the at least one survey server, wherein the SPA enables the at least one client to express opinion on said scale using at least one input device of the client device, whereby a pixel position corresponding to the position of the client input selection comprises a rating for the selected subject.

5. The apparatus according to claim 1, wherein the client device display displays, for each rating of said plurality of subjects, a connector attaching the drop position to each rating image.

6. The apparatus according to claim 1, wherein the client device records each change of rating for each of the plurality of rating images, thereby facilitating the acquisition of data to support conjoint analysis that is otherwise more costly to acquire.

7. The apparatus according to claim 1, wherein for any one of said plurality of P(x), all of the evaluation occurs in the client device.

8. The apparatus according to claim 1, wherein for any one of said plurality of P(x), the evaluation in the client device occurs only in the client device.

* * * * *